(12) United States Patent
Kuok et al.

(10) Patent No.: US 6,790,464 B2
(45) Date of Patent: Sep. 14, 2004

(54) HERBAL COMPOSITIONS FOR PROSTATE CONDITIONS

(75) Inventors: Koon Yong Kuok, Wong Chuk Hang (HK); Hien Ly, Phnom Penh (KH)

(73) Assignee: Healthaid Enterprise Pte. Ltd., Singapore (SG)

( * ) Notice: Subject to any disclaimer, the term of this patent is extended or adjusted under 35 U.S.C. 154(b) by 0 days.

(21) Appl. No.: 10/345,158

(22) Filed: Jan. 16, 2003

(65) Prior Publication Data

US 2004/0142001 A1 Jul. 22, 2004

(51) Int. Cl.⁷ .................. A61K 35/78; A61K 35/84
(52) U.S. Cl. .................. 424/725; 424/773; 424/775; 424/777; 424/195.16
(58) Field of Search .................. 424/725, 195.16, 424/773, 775, 777

(56) References Cited

U.S. PATENT DOCUMENTS

| | | |
|---|---|---|
| 4,258,037 A | 3/1981 | Juvin |
| 4,613,591 A | 9/1986 | Aburada et al. |
| 4,618,495 A | 10/1986 | Okuda et al. |
| 5,417,979 A | 5/1995 | Fan et al. |
| 5,543,146 A | 8/1996 | Perez |
| 5,665,393 A | 9/1997 | Chen et al. |
| 5,721,134 A | 2/1998 | Lee et al. |
| 5,736,144 A | 4/1998 | Gideon |
| 6,197,309 B1 | 3/2001 | Wheeler |

FOREIGN PATENT DOCUMENTS

| | | | |
|---|---|---|---|
| CN | 1083368 | * | 3/1994 |
| CN | 1166355 | * | 12/1997 |
| CN | 1185322 | * | 6/1998 |
| CN | 1208643 | * | 2/1999 |
| CN | 1294013 | * | 5/2001 |

* cited by examiner

Primary Examiner—Christopher R. Tate
(74) Attorney, Agent, or Firm—Piper Rudnick LLP; Steven B. Kelber

(57) ABSTRACT

Methods and compositions are disclosed for prevention or treatment of prostate disorders and ameliorating symptoms thereof, including prostatitis, benign prostate hyperplasia and prostatic carcinoma. The methods comprise administering a composition of matter comprising the following herbal and other components: Radix Asparagi; Radix Angelicae Pubescentis; Radix Trichosanthis; Radix Scuttellariae; Radix Angelicae Sinensis; Radix Dipsaci; Cortex Eucommiae; Medulla Junci; Rhizoma Anemarrhenae; Caulis Akebiae; Herba Dianthi; Semen Plantaginis; Cortex Phellodendri (fried); Radix et Rhizoma Rhei; Rhizoma seu Radix Notopterygii; Olibanum; Fructus Gardeniae; Radix Astragali seu Hedysari; Rhizoma Cimicifugae; Radix Bupleuri; Myrrha; Gypsum Fibrosun; Radix Rehamanniae (crude); Folium Pyrrosiae; Rhizoma Acori Graminei; Rhizoma Dioscoreae Hypoglaucae; Radix Linderae; Herba Cistanche; Radix Paeoniae Rubra; Rhizoma Dioscoreae; Semen Euryales; Cortex Mouton; Polyporus Umbellatus; Radix Rehmanniae Praeparata; Medulla Tetrapanacis; Semen Coicis; Fructus Horedi Germinatus (Poria); Radix Aconiti Praeparata; Rhizoma Alismatis; Cortex Cinnamomi; Herba Asari; Radix Glycyrrhizae; Stigma Maydis; *Phaseolus Radiatus* L., and optionally, *Ganoderma Lucidum*.

17 Claims, 15 Drawing Sheets

HERBAL COMPOSITIONS FOR PROSTATE CONDITIONS

BACKGROUND OF THE INVENTION

1. Field of the Invention

The present invention relates generally to compositions and methods of using them for prevention or treatment of disorders of the prostate gland. More specifically, the invention relates to compositions and methods for prevention or treatment of prostate carcinoma, benign prostate hyperplasia or prostatitis, and for relieving symptoms and improving objective signs of such prostate disorders.

2. Background of the Technology

Currently, thousands of drugs commonly used and prescribed today are either derived from a plant source or contain chemical imitations of a plant compound. Many of these medicinal formulations contain herbal components or extracts from herbs. Technically speaking, an herb is a small, non-woody (i.e., fleshy stemmed), annual or perennial seed-bearing plant in which all the aerial parts die back at the end of each growing season. As the word is more generally used and as it is used herein, an herb is any plant or plant part which has a medicinal use. Thus, the term herb is also generally used to refer to the seeds, leaves, stems, flowers, roots, berries, bark, or any other plant parts that are used for healing.

Traditionally, dietary supplements referred to products made of one or more of the essential nutrients, such as vitamins, minerals, and protein. Passage of the Dietary Supplement Health and Education Act of 1994 (DSHEA) broadened the definition to include, with some exceptions, any product intended for ingestion as a supplement to the diet. This includes vitamins; minerals; herbs, botanicals, and other plant-derived substances; and amino acids (the individual building blocks of protein) and concentrates, metabolites, constituents and extracts of these substances. Dietary supplements are usually in a dosage form such as capsules, tablets, liquids, powders, soft gels, etc. and generally are not represented as a conventional food or as a sole item of a meal or of the diet (Dietary Supplement Health and Education Act of 1994, Section Three).

The passage of DSHEA established a new regulatory framework for dietary supplements (Dietary Supplement Health and Education Act, Public L. No. 103-417, 108 Stat. 4325 (1994)). DSHEA, which amends the Federal Food Drug and Cosmetic Act, allows supplement manufacturers to make certain limited statements of nutritional support for dietary supplements including a statement that: (1) claims a benefit to a classical nutrient deficiency disease and discloses the prevalence of such disease in the U.S.; (2) describes the role of a nutrient or dietary ingredient intended to affect the structure or function in humans; (3) characterizes the documented mechanism by which a nutrient or dietary ingredient acts to maintain such structure or function; or (4) describes general well-being from consumption of a nutrient or dietary ingredient (Dietary Supplement Health and Education Act, Public L. No. 103-417 §6, 108 Stat. 4325, 4329 (1994)).

Dietary supplements are available widely through many commercial sources including health food stores, grocery stores, pharmacies, and by mail. Historically in the United States, the most prevalent type of dietary supplement was a multivitamin/mineral tablet or capsule that was available in pharmacies by prescription or "over the counter." Supplements containing strictly herbal preparations were less widely available. Currently in the United States, a wide array of supplement products are available and they include vitamin, mineral, other nutrients, and botanical supplements as well as ingredients and extracts of animal and plant origin.

The prostate gland (or prostate) is a walnut-sized, mucous-producing organ in males that lies just below the urinary bladder. The prostate typically grows and enlarges throughout life. The only known function of the prostate is to produce a secretion that nourishes and protects the sperm during reproduction. The urethra, the canal that in most mammals discharges urine from the bladder, passes through the prostate gland. Unfortunately, this anatomical feature creates problems, often associated with difficulty in urination, as males age.

In men, the prostate gland is the source of several common disorders including prostatitis and benign prostatic hyperplasia (BPH), wherein the prostrate gland becomes inflamed or enlarged. Prostatitis is defined as an inflammation or infection of the prostate gland. While prostatitis may be acute, associated with systemic findings of fever, chills and rigors, most cases of prostatitis are chronic and tend to be incurable with relatively frequent recurrences despite optimal standard therapy. Chronic prostatitis (inflammation or infection of the prostate) is common to all adult men. It is associated with virtually all cases of prostate cancer and is present in every prostate biopsy regardless of other findings. Chronic prostatitis may not cause significant symptoms in many men, but in others it can be a devastating disease that severely affects the quality of life of those afflicted. It is difficult to diagnose and even more difficult to treat.

The most common symptom of chronic prostatitis is pelvic pain, followed by various voiding symptoms, impotence, and infertility. Pain from prostatitis is usually located in the groin, testicles, and penis, just above the rectum or in the suprapubic area over the bladder. Pain is frequently associated with ejaculation. Typical voiding symptoms produced by prostatitis include getting up at night to void (nocturia), frequency and urgency of urination, incomplete voiding, decreased force of the urinary stream, intermittency of the stream and a need to push or strain to void. Impotence or erection difficulties and male infertility are also associated with prostatitis.

U.S. Pat. No. 6,197,309 to Wheeler discloses a prostate formula composition said to provide an all-natural, non-surgical preventative of or improvement to disorders of the prostate gland, particularly, prostatitis, and for relieving symptoms and improving objective signs of prostatitis. The formula of the composition preferably includes the following ingredients each in a therapeutically effective amount: Vitamin C, Vitamin B6, Vitamin E, zinc, glycine, L-alanine, Glutamic acid, Saw palmetto, Pygeum extract, Pumpkin seed, Stinging nettle, Echinacea, garlic, Ginkgo leaves, and selenium.

According to Wheeler, supra., a wide variety of therapies for prostatitis are available, but few actually work in more than a small percentage of cases. None of the standard treatments is able to improve the health and well being of the prostate.

In the treatment of prostatitis, physicians have traditionally recommended everything from doing nothing to multiple and extended courses of antibiotics, other drugs, and lifestyle changes. Those patients who truly have an identifiable infection of the prostate benefit from antibiotics. These need to be continued for at least 6–12 weeks and, in some cases, long-term or indefinite antibiotic suppression therapy is necessary.

BPH occurs naturally in most males over 50 years of age. At this age, the male body begins to transform testosterone (male sex hormone) into dihydroxytestosterone (DHT) at higher levels within the prostate. This is primarily due to the higher levels of the enzyme reductase, which causes the conversion of testosterone to DHT. DHT has a tendency to bind to prostatic receptor cells, which ultimately results in prostate enlargement. It is usually a benign condition, and therefore, in some cases there is no need for surgery. However, enlargement of the prostate gland can cause many uncomfortable and annoying symptoms. Worsening symptoms may require prostate surgery. Nearly 400,000 prostate surgical procedures are performed annually to treat enlarged prostates. Numerous laboratories are conducting research in an attempt to find a cure for BPH.

Further, according to Wheeler, supra., treatments for prostate disorders include alpha blockers, e.g., HYTRIN (terazosin HCl, Abbott Laboratories, Abbott Park, Ill.), CARDURA (Roerig Pharmaceuticals, Alexandria, Va.) and FLOMAX (tamsulosin HCl, Boehringer Ingelheim Pharmaceuticals, Ridgefield, Conn.), which are designed to relax the muscle tension in the prostate and improve urinary flow. They do tend to improve voiding difficulties and relax tension in the prostate. However, they are expensive, need to be taken indefinitely in high doses, may often have significant side effects and do not cure the underlying problem or prevent recurrences.

There are also other treatments for prostate disorders. For example, PROSCAR (finasteride, Merck Human Health, White House Station, N.J.) can shrink prostate tissue, but there is no proof it helps in the treatment of prostatitis. Allopurinol, a drug that reduces uric acid levels in the body, has been used to treat prostatitis based on the theory that uric acid crystals may form in the prostate and cause inflammation. Anti-inflammatory agents, such as ibuprofen, and hot sitz baths have been helpful in treating the discomfort caused by prostatitis in many patients, but neither of these treatments actually cures the disease and the benefits wear off rapidly.

Irritative voiding symptoms may be relieved by bladder relaxing agents such as oxybutynin (DITROPAN Alza Corporation, Palo Alto, Calif.), while antidepressants such as amitriptyline (ELAVIL AstraZeneca, Wilmington, Del.) have been helpful in various chronic pain conditions such as prostatitis associated with depression. Biofeedback, behavioral therapy, referral to a pain clinic and psychological treatment have all been recommended for patients with prostatitis and occasionally offer some relief to selected individuals. For the most part, current treatment methods for prostatitis are generally rather disappointing.

Prostatic massage plus antibiotics has been used with some success. However, proponents of prostatic massage (championed in the Philippines) have little reproducible data to support their methods. Other drawbacks include intense discomfort/pain at the time of massage, the need for accurate cultures of the prostatic fluid, and a dependence on antibiotics to ultimately effect the cure.

There are natural elements that have known benefits in treating enlargement of the prostate gland and prostatitis. It is widely accepted that zinc has positive effects in reducing an enlarged prostate, but studies have indicated that zinc administered orally does not reach prostatic tissue very effectively. Therefore, the prostate does not reap its full benefits. Other studies have shown that Pygeum africanum extract has definite effects in reducing the size of the prostate. Extensive studies have shown that Saw palmetto (*Serenoa repens*) effectively reduces the size of the enlarged prostate and restores function. Another natural product known to produce beneficial effects on the enlarged prostate is pumpkin seed. Pumpkin seeds have been used as a folk remedy for centuries, and it is believed that Hungarian gypsies, Ukrainians and Transylvanians do not suffer from BPH because they eat pumpkin seeds from childhood as part of their daily diet. Additionally, according to Wheeler, supra., the Chinese use a combination of three amino acids: glycine, L-alanine, and glutamic acid, to treat disorders of the prostate. PROSTAMAX (Hankintatukku Natural Products Co., Helsinki, Finland) is a prostate formula on the market, having a per tablet formula of Vitamin C, 10 mg; Vitamin B6, 10 mg; Vitamin E (succinate), 5 IU; zinc chelate, 10 mg; L-glycine, 120 mg; alanine, 120 mg; Saw palmetto, 106 mg; *Pygeum africanus* extract, 10 mg; *Pygeum africanus* herb, 20 mg; pumpkin seed, 200 mg; Stinging nettle leaves, 75 mg; Echinacea, 25 mg; Ginkgo biloba, 20 mg; Wild yam, 20 mg; and *Uva ursi*, 10 mg.

U.S. Pat. No. 5,736,144 to Gideon describes a medicinal tea made from radishes. The tea is used as an anti-microbial or anti-inflammatory agent and is reportedly effective in treating prostatitis.

U.S. Pat. No. 4,258,037 to Juvin describes a therapeutic composition said to be useful for the treatment of both male and female urogenital disorders such as prostatic disorders and bartholinitis. The composition contains Pygeum or other extracts of the trees of the Rosaceae-family, together with a mono-aminated amino acid such as glycine, L-glutamic acid or L-alanine.

U.S. Pat. No. 5,543,146 to Perez describes a dietary supplement composition for alleviating the symptoms associated with enlargement of the prostate gland. The composition includes pumpkin seeds, zinc, magnesium, vitamin E, Saw palmetto, and *Pygeum africanum*, but does not include stinging nettle, zinc, garlic, ginkgo, glutamic acid, alanine, glycine, Echinacea and *Uva ursi*.

Prostate carcinoma is a major cause of death among men. In the U.S., recent estimates indicate that well over 300,000 men are diagnosed with prostate cancer each year. While many of the small, localized prostate cancer appear not to be life-threatening, those that spread to other sites in the body are almost invariably fatal. Conventional treatment includes radical prostactomy, nerve-sparing prostatectomy, external-beam radiation, seed radiation, cryotherapy and hormone therapy. Each of these therapies has serious side effects and other limitations, and recurrence frequently occurs.

Serum PSA (Prostate Specific Antigen) is a diagnostic parameter that has been used to monitor the stages of prostrate cancer development and the progress of the therapy. Serum PSA measures the substance emitted both by the normal prostate gland and by cancerous tissue in the prostate gland. With normal prostate gland, PSA reads between 0 to 4. Elevated PSA (higher than 5) indicates a sign of prostate carcinoma, benign prostate hyperplasia or prostatitis. The higher the PSA reading, the larger the volume of the cancer.

U.S. Pat. No. 5,665,393 to Chen. et al. discloses an herbal composition for treating prostate conditions comprising material from the following herbs: Panax pseudo-ginseng Wall, *Isatis Indigotica* Fort, *Ganoderma lucidum* Karst, *Dendranihema morifolium* Tzvel, *Glycyrrhiza glabra* L., *Scutellaria baicalensis* Georgi, *Rabdosia rubescens*, *Serenoa repens*. Preferably, the material from each of such herbs is an alcohol extract of dried, cut plants and of the Panax. The pseudo-ginseng Wall and each of the other materials are present in a dried, weight-to-weight range of about 1:1–6. The composition is administered orally or by suppository. Chen further discloses combining administration of the herbal composition with administration of a therapeutically effective amount of an anticancer compound effective for prostate cancer, such as luteinizing hormone releasing hormone, estrogen, antiandrogen, gonadotrophin-releasing hormone and synthetic analogs thereof which have hormone activity, or of other agents generally effective for treatment of infections or malignancies, such as antibiotics, antimetabolites and cytotoxic agents.

U.S. Pat. No. 5,417,979 to Fan, et al., discloses a combination of the herbs *Ganoderma lucidum* Karst, *Rabdosia rubescens* and *Glycyrrhiza glabra* L. with other herbs for treatment of cancers other than prostate cancer.

U.S. Pat. No. 5,721,134 to Lee, et al. discloses *Ganoderma lucidum* KCCM 10045 which produces proteoglycan (G009) having an effect of antitumor immunity.

U.S. Pat. No. 4,613,591 to Aburada, et al. discloses an adminiculum for increasing the antitumor activities of mitomycin C and doxorubicin hydrochloride and decreasing the side effects associated with their use comprising an aqueous or aqueous organic solvent extract of a crude preparation of Astragali radix, Cinnamomi cortex, Rehmanniae radix, Paeoniae radix, Cnidii rhizoma, *Atractylodis lanceae* rhizoma, Angelicae radix, Ginseng radix, Hoelen and Glycyrrhizae radix. Also disclosed are a method for preparing this adminiculum and a method for its use. In addition, compositions and methods for treating tumor-bearing patients are disclosed.

U.S. Pat. No. 4,618,495 to Okuda, et al. discloses a composition for reducing cancer symptoms by improving lipid metabolism and eliminating or reducing anorexia in tumor-bearing patients through inhibition of the lipid degradation-promoting action of toxohormone L, which comprises an aqueous or aqueous organic solvent extract of one or more crude preparations selected from the group consisting of Astragali radix, Cinnamomi cortex, Rehmanniae radix, Paeoniae radix, Cnidii rhizoma, *Atractylodis lanceae* rhizoma, Angelicae radix, Ginseng radix, Hoelen and Glycyrrhizae radix. Also diclosed are a method for preparing such a composition, and a method for reducing cancer symptoms using the composition.

There is thus a need for compositions and methods for prevention and treatment of disorders of the prostate gland, particularly for prevention or treatment of prostate carcinoma, benign prostate hyperplasia or prostatitis, for relieving symptoms and improving objective signs of such prostate disorders, and for maintaining prostate health.

SUMMARY OF THE INVENTION

A primary object of the present invention is to provide a composition having beneficial effects in preventing and treating prostate disorders including prostatitis, benign prostate hyperplasia and prostatic carcinoma.

It is also an object of the invention to provide a composition that is beneficial to various symptoms of prostate disorders, including elevated blood levels of Prostate Specific Antigen (PSA) and irritative voiding symptoms such as getting up at night to void (nocturia) and otherwise excessive frequency and urgency of urination.

It is a further object of the invention to provide a composition for preventing and treating prostate disorders that has all natural ingredients, has no adverse side effects, has no interactions with any medication, and may be taken orally in solid or liquid form or in various other forms.

Yet another object of the invention is to provide a method of preventing and treating prostate disorders and of maintaining prostate health using compositions of this invention.

These and other objects are satisfied by the present invention providing a composition comprising herbs and fungi or extracts thereof, which is useful to prevent or treat prostate disorders and which can also be used as a dietary supplement to maintain or improve prostate health. Combinations of herbs and fungi and extracts thereof, according to the invention, profoundly improve the conditions of patients with prostate disorders including prostatitis and prostate cancer, and alleviate symptoms such as elevated serum PSA levels and nocturia and otherwise excessive frequency and urgency of urination.

One embodiment of the composition of the invention comprises at least 44 particular herbal or other natural components, or extracts thereof. Preferably, the composition further comprises *Ganoderma Lucidum*. Preferably, material from each of the herbs or fungi is an aqueous extract of dried, cut plant or fungal parts. It is particularly preferred that the herbal components and each of the other materials are present in relative amounts (dried weight-to-weight ratios) that lie within particular ranges disclosed herein. Composition of the invention are preferably provided in an ingestible form, such as, for example, a powder, capsule or tablet.

The invention further provides methods of treating prostate disorders including prostatitis, benign prostate hyperplasia and prostatic carcinoma. One such method is for treating prostate cancer in an individual in need thereof which comprises administering a therapeutically effective amount of an herbal composition described herein. Preferably, the invention method further comprises administering a therapeutically effective amount of an anticancer compound effective for prostate cancer, selected from the group consisting of luteinizing hormone releasing hormone, estrogen, antiandrogen, gonadotrophin-releasing hormone and synthetic analogs thereof which have hormone activity. The invention also preferably provides such a method further comprising administering a therapeutically effective amount of a compound selected from the group consisting of antibiotics, antimetabolites and cytotoxic agents.

One aspect of the present invention, therefore relates to a composition comprising the following herbal and other components: Radix Asparagi; Radix Angelicae Pubescentis; Radix Trichosanthis; Radix Scuttellariae; Radix Angelicae Sinensis; Radix Dipsaci; Cortex Eucommiae; Medulla Junci; Rhizoma Anemarrhenae; Caulis Akebiae; Herba Dianthi; Semen Plantaginis; Cortex Phellodendri (fried); Radix et Rhizoma Rhei; Rhizoma seu Radix Notopterygii; Olibanum; Fructus Gardeniae; Radix Astragali seu Hedysari; Rhizoma Cimicifugae; Radix Bupleuri; Myrrha; Gypsum Fibrosun; Radix Rehamanniae (crude); Folium Pyrrosiae; Rhizoma Acori Graminei; Rhizoma Dioscoreae Hypoglaucae; Radix Linderae; Herba Cistanche; Radix Paeoniae Rubra; Rhizoma Dioscoreae; Semen Euryales; Cortex Mouton; Polyporus Umbellatus; Radix Rehmanniae Praeparata; Medulla Tetrapanacis; Semen Coicis; Fructus Horedi Germinatus (Poria); Radix Aconiti Praeparata; Rhizoma Alismatis; Cortex Cinnamomi; Herba Asari; Radix Glycyrrhizae; Stigma Maydis; and Phaseolus Radiatus L. In a preferred embodiment, this composition further comprises *Ganoderma Lucidum*.

Additional embodiments of the compositions of the present invention include a composition described above, further comprising at least one herbal or other component selected from the following group of components: Bulbus Lilii; Citri Reticulatae Viride; Cortex Moutan Radicis; Cortex Lycii Radicis; Faecs Trogropterori; Flos Lonicerae; Fructus Alpiniae Oxyphyllae; Fructus Aurantii Immaturus; Fructus Cnidii; Fructus Corni; Fructus Schisandrae; Fructus Arctii; Herba Cynomorii; Herba Epimedii; Herba Leonuri; Herba Polygoni Avicularis; Radix Achyranthis Bidentatae; Radix Aconiti Kusnezoffii; Radix Angelicae Dahuricae; Radix Aucklandiae; Radix Clematidis; Radix Codonopsis Pilosulae; Radix Gentianae Macrophyllae; Radix Ophiopogonis; Radix Paeoniae Alba; Radix Polygalae; Radix Stephaniae Tetrandrae; Ramulus Cinnamomi; Rhizoma Atractylodis; Rhizoma Belamcandae; Rhizoma Corydalis; Rhizoma Ligustici Chuanxiong; Rhizoma seu Radix Nototerygii; Rhizoma Zingiberis Recens; Semen Biotae; Semen Cuscutae; Semen Dolichoris Album; Semen Pharbitidis; Semen Persicae; Spica Prunellae; and Stigma Maydis.

Preferably, compositions of the present invention comprise an aqueous or alcohol or aqueous-alcohol extract of each specified herbal component. Other forms of the specified components are also contemplated, however, including mixtures of dried forms of the specified crude components, such as whole dried plants or plant parts, or powders of ground dried plants or part, or powders of extracts or decoctions of plants and other components.

In a particularly preferred embodiment, the invention composition comprises an aqueous extract of the following herbal and other components in the specified ratios of dry weights compared to the dry weight of the least abundant component (as recited in Table 2, supra.): Radix Asparagi (6:1); Radix Angelicae Pubescentis (6:1); Radix Trichosanthis (9:1); Radix Scuttellariae (4:1); Radix Angelicae Sinensis (1:1); Radix Dipsaci (1:1); Cortex Eucommiae (1:1); Medulla Junci (1:1); Rhizoma Anemarrhenae (4:1); Caulis Akebiae (8:1); Herba Dianthi (8:1); Semen Plantaginis (6:1); Cortex Phellodendri (fried) (8:1); Radix et Rhizoma Rhei (4:1); Rhizoma seu Radix Notopterygii (1:1); Olibanum (1:1); Fructus Gardeniae (7:1); Radix Astragali seu Hedysari (15:1); Rhizoma Cimicifugae (4:1); Radix Bupleuri (4:1); Myrrha (1:1); Gypsum Fibrosun (18:1); Radix Rehamanniae (crude) (15:1); Folium Pyrrosiae (9:1); Rhizoma Acori Graminei (6:1); Rhizoma Dioscoreae Hypoglaucae (6:1); Radix Linderae (6:1); Herba Cistanche (1:1); Radix Paeoniae Rubra (6:1); Rhizoma Dioscoreae (9:1); Semen Euryales (6:1); Cortex Mouton (1:1); Polyporus Umbellatus (6:1); Radix Rehmanniae Praeparata (1:1); Medulla Tetrapanacis (6:1); Semen Coicis (8:1); Fructus Horedi Germinatus (Poria) (9:1); Radix Aconiti Praeparata (6:1); Rhizoma Alismatis (6:1); Cortex Cinnamomi (3:1); Herba Asari (4:1); Radix Glycyrrhizae (3:1); Stigma Maydis (18:1); Phaseolus Radiatus L (31:1); and *Ganoderma Lucidum* (1:1).

Compositions of the invention, particularly compositions comprising extracts of the specified components, optionally further comprise a pharmaceutically acceptable carrier, diluent or additive, for use as a pharmaceutical composition. In another aspect, the invention provides a dietary supplement comprising a composition of the invention.

Preferred embodiments of compositions according to the present invention provide a composition of matter comprising a mixture of the herbal and other components listed in Table 2, wherein the components are present in the mixture in amounts such that the mixture is effective in a mammal for preventing or treating prostate disorders including prostatitis, benign prostate hyperplasia and prostatic carcinoma. Preferably, mammal in which this composition is effective is a human being susceptible to or suffering from a prostate disorder. In particular, such mixtures are effective for reducing serum levels of Prostate Specific Antigen (PSA) that are elevated above normal and for reducing irritative voiding symptoms of prostatitis.

In preferred embodiments of the invention composition, the mixture is effective for ameliorating at least one effect of a prostate carcinoma in a human or other mammal having such a tumor. Ameliorated effects of a prostate carcinoma include but are not limited to reducing the growth rate or mass of the carcinoma.

In another aspect, the present invention provides a method for prevention or treatment of prostate disorders in a mammal including prostatitis, benign prostate hyperplasia and prostatic carcinoma, comprising administering to the mammal a composition of matter of the invention, periodically for a time sufficient to achieve prevention or treatment of the prostate disorder in the mammal. In one embodiment of this method, the disorder is prostatic carcinoma and the administering is performed before surgery to remove the carcinoma, to reduce the tumor size and to cause better separation of the tumor from surrounding normal tissue. Preferably, the administering of an invention composition periodically is conducted once or twice daily, or at least about three to four times a week.

The method of treating prostatic carcinoma optionally further comprises administering a therapeutically effective amount of an anticancer compound effective for prostate cancer, selected from the group consisting of luteinizing hormone releasing hormone, estrogen, antiandrogen, gonadotrophin-releasing hormone and synthetic analogs thereof which have hormone activity, or a therapeutically effective amount of a compound selected from the group consisting of antibiotics, antimetabolites and cytotoxic agents. Method of using each of these agents for treating prostate cancer, prostatitis or other prostate conditions are well known in the art.

In yet another aspect, the invention provides a method of ameliorating symptoms associated with prostate disorders in a mammal, preferably a human being suffering from such a disorder, including prostatitis, benign prostate hyperplasia and prostatic carcinoma. This method comprises administering to the mammal a composition of matter of the invention periodically for a time sufficient to achieve the desired amelioration.

DETAILED DESCRIPTION OF THE INVENTION

Figure 1:
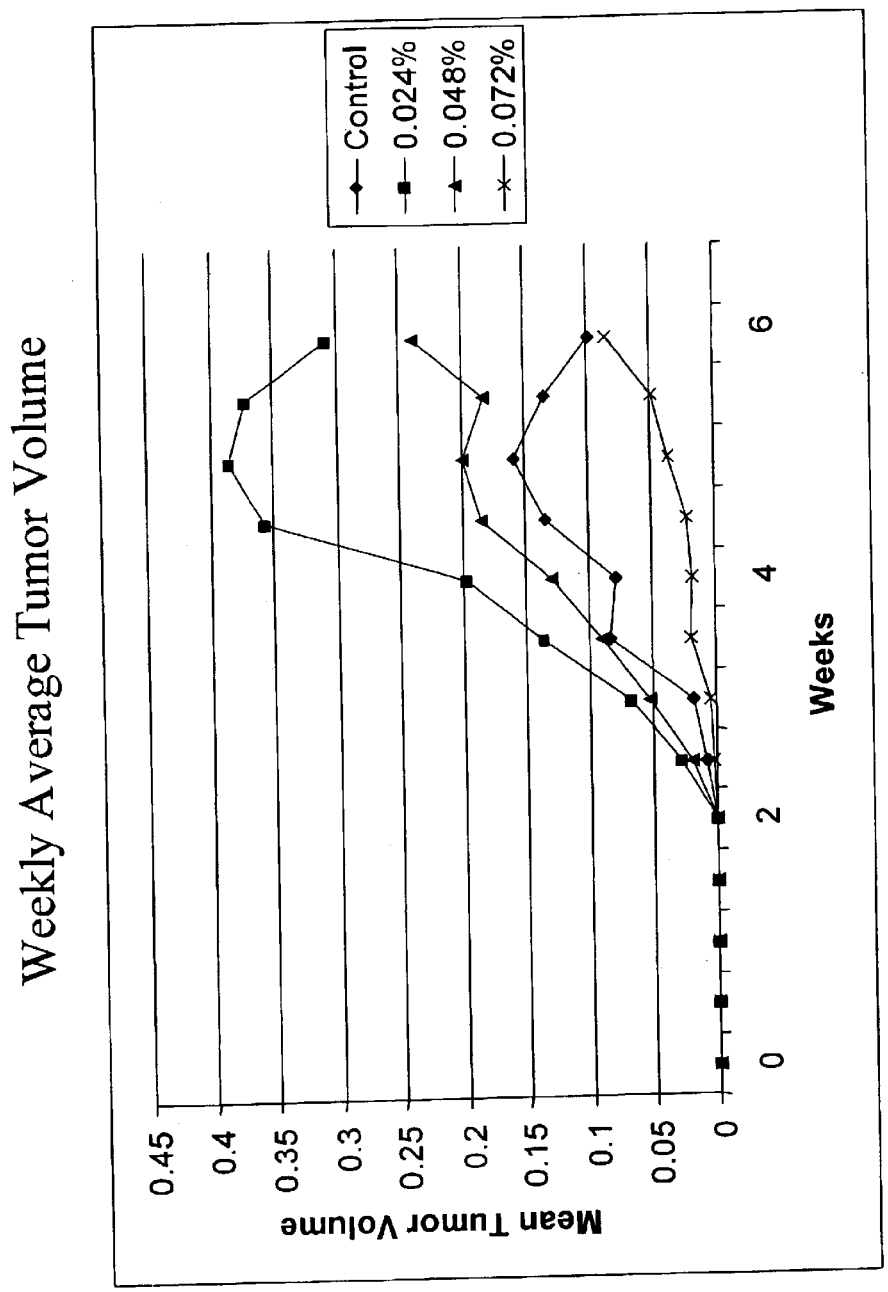
FIG. 1 shows the reduction in weekly average tumor volume of mice injected with human prostate (DU145) tumor cells in three groups fed differing amounts of an herbal extract of the present invention, compare to the control group during the course of a six-week study.

The present invention is based in part upon the finding that aqueous extracts crude preparations of various combinations of components selected from the group listed in Table 1, below, have beneficial effects for prostate disorders including prostatitis, benign prostate hyperplasia and prostatic carcinoma. During a long-term prostate disease research effort, the inventors of the present invention formulated numerous herbal-, animal- and mineral-based compositions and assessed their effectiveness in treating irritative voiding symptoms, elevated serum PSA levels and prostate cell tumors in human subjects and/or animal models.

The compositions of the present invention were developed as a result of many clinical assessments using various herbal-based compositions to treat prostate disease symptoms. As discussed herein, the compositions of the present invention can be used instead of or in addition to conventional drugs to control or relieve the symptoms of prostate conditions during their active stages and to prevent prostate conditions before the become active. Initial studies by the inventors led to the discovery of effective compositions comprising various combinations of components listed in Table 1, below. Subsequent experimentation by the inventors led to the discovery of a preferred composition comprising the components described in Table 2, below.

Herbal compositions of the present invention include components from plant species of the various genera listed in Table 1, below. The compositions of the invention can also include various additional ingredients, such as minerals (e.g., calcium sulfate), animal products or pharmaceutically acceptable carriers and/or fillers. Individual components of the composition, and extracts thereof, are described in greater detail below.

Extracts of compositions of the present invention can be produced by extracting "crude preparations" of components selected from the group consisting of the components listed in Table 1. The crude preparations employed according to the invention may be obtained from commercial sources or by methods well known in the art of Chinese herbal medicine. Quality standards for most of the herbal and other components used in compositions according to the present invention are set forth, for instance, in the Chinese Pharnacopcia (1990).

Typically, an herbal composition of the invention is prepared from leaf and/or root and/or bark portions of several specific types of plants that, in combination, have marked and significant effects in the prevention and treatment of prostate conditions. Numerous herbal formulations and extracts, including most or all of the components indicated in Table 1, were examined. Following experimentation, the preferred ingredient mixture indicated in Table 2 was derived. The Examples below provide detailed scientific results that can be used by a skilled artisan to prepare and administer the compositions of the present invention.

Crude preparations used in the present invention are typically made from pure natural Chinese herbs which are individually washed, dried and ground into fine powder, then extracted, for example, with medical ion exchange water (and/or alcohol or an aqueous alcohol solution) separately, and then mixed together. Alternatively, the herbs and other components may be mixed prior to extraction, or the components may be sequentially extracted using one or more volumes of solvent. In any event, the resultant mixture is typically dried, smashed, screened, and then mixed with any additional components. The final composition can be incorporated into any means for a convenient mode of administration, with oral intake being the preferred administration method, as exemplified herein.

More specifically, dried herbal components such as Radix Stephaniae Tetrandrae may be ground into fine powder to provide a crude preparation. Alternatively, herbs may be decocted (i.e., boiled-down) with water, for instance, twice, first using ten times water by weight as the total weight of the herbs, then using eight times as much water by weight as the total herbal weight. The time for each decoction step preferably is about one to about twelve hours, more preferably about two hours. The material resulting from the decoctions is then mixed and filtered (and, if necessary, concentrated, e.g., by evaporation or lyophilization) so as to concentrate the filtrate to a heavy paste. Powders of other components may then be added to the heavy paste, if desired, and the resultant product can then be mixed, dried, pulverized, sieved and mixed again until desirably homogeneous. The resulting powder can be placed into containers or capsules for oral administration to patients.

An extract of the invention also can be obtained by extracting a mixture of one or more of the above crude preparations or by mixing extracts from each crude preparation. For instance, one or more crude preparations may be extracted with water alone or water comprising 5–50 v/v % of a water miscible organic solvent such as an alcohol (preferably ethanol), filtering the obtained solution and optionally drying by conventional drying means, such as spray-drying, freeze drying or concentration drying. Extraction can be carried out at room temperature or with heating; heating at 80°–100° C. is preferred. The extract can be used per se, in liquid form, or prepared in powder, granule, tablet, or capsule form mixed with conventional adjuvants or additives. The extract or active ingredients therein can optionally be purified by conventional means, such as dialysis or chromatography. A preferred method of producing extracts of the invention is exemplified in Example 1, below.

Compositions of the present invention find particular application as dietary supplements for the treatment of certain symptoms usually associated with various prostate conditions and diseases, especially prostatitis and benign prostatic hyperplasia (BPH), as well as prostate carcinoma. However, compositions of the invention are useful for the treatment of prostatitis-like symptoms regardless of the actual cause of the condition and regardless of the U.S. Food and Drug Administration (FDA) category in which the compositions are classified. Utilizing the results provided herein, a skilled artisan can readily practice and develop the dietary and therapeutic methods outlined herein and in the appended claims.

Chinese herbal components that may be included in compositions of the invention are listed in Table 1, below, by medicinal name and common and botanical source name(s), along with two non-herbal components (Gypsum Fibrosum, for which the listed source is mineral (calcium sulfate), and Faecs Trogropterori, for which the listed source is animal (flying squirrel feces).

TABLE 1

Herbal and Other Components and Sources

| Medicinal Name | Common Source Name (Botanical Source Name) |
|---|---|
| Bulbus Lilii | Lilly bulb (*Lilium brownii* var. *viridulum* Baker; *Lilium pumilum* DC; *Lilium lancifolium* Thunb.) |
| Caulis Akebiae | Clematis stem (*Caulis akebia trifoliata, Akebia quinata, Aristolochia manchuriensis*, Ranunculaceae) |
| Citri Reticulatae Viride | Fruit or pericarp (*Citrus reticulata* Blanco, family Rutaceae) |
| Cortex Moutan Radicis | Mouton (root) bark (*Paeonia suffruticosa* Andr. (family Ranunculaceae) |
| Cortex Cinnamomi | Cassia Bark |
| Cortex Eucommiae | Dried bark of hardy rubbertree (*Eucommia ulmoides* Oliv, family Eucommiaceae) |
| Cortex Lycii Radicis | Wolfberry bark (*Lycium chinense* Mill., or *Lycium barbarum* L., family Solanaceae) |
| Cortex Phellodendri (fried) | Corktree bark (*Phellodendron amurense* Rupr. or *P. Chinese* Scheid., family Rutaceae) |
| Faecs Trogropterori | Rhizoma Trogopterorum; Wu Ling Zhi; flying squirrel feces (*Trogoterus xanthipes* Milne-Edwards, family Petauristidae) |
| Flos Lonicerae | Honeysuckle flower; Lonicera flower (*Lonicera japonica* Thunb. L.; *Lonicera hypoglauca* Miq.; *Lonicera confusa* DC.; *Lonicera dsystyla* Rehd) |
| Folium Pyrrosiae | Pyrrosia leaf (*Pyrrosia lingua* (Thunb.) Farwell, *P. sheareri* (Bak.) Ching, and *P petfolosa* (Christ) Ching, family Polypodiaceae) |
| Fructus Alpiniae Oxyphyllae | Black cardamom, bitter cardamom (*Alpinia oxyphylla* Miq.) |
| Fructus Aurantii Immaturus | Immature bitter orange fruit (*Citrus aurantium* L.; *Citrus sinensis* Osbeck) |
| Fructus Cnidii | Cnidium fruit (*Cnidium monnieri* (L.) Cuss. |
| Fructus Corni | Cornus fruit, Dogwood fruit (*Cornus officinalis* Sieb. et Zucc.) |
| Fructus Gardeniae | Cape Jasmine fruit |
| Fructus Horedi Germinatus (Poria) | Germinated barley (malt) |

TABLE 1-continued

Herbal and Other Components and Sources

| Medicinal Name | Common Source Name (Botanical Source Name) |
|---|---|
| Fructus Schisandrae | Schisandra fruit (*Schisandra chinensis* (Turcz.) Baill.; *Schizandra sphenanthera* Rehd. et Wils.) |
| Fructus Arctii | Arctium fruit, Burdock fruit (*Arctium lappa* L.) |
| Ganoderma Lucidum | Ganoderma Lucidum, Royal Gano (reishi, lingzhi, biladi top, young ji; basidiomycete, lamellaless fungus, family Polyporaceae) |
| Gypsum Fibrosun | Calcium sulfate |
| Herba Asari | (Asari) Manchurian wild ginger; dried herb (*Asarum heterotropoides* Fr. var. *mandshuricum* (Maxim.) Kitag., *Asarum sieboldii* Miq. var seoulense Nakai or *Asarum sieboldii* Miq., family Aristolochiaceae) |
| Herba Cistanche | Dried fleshly stem with scales of desert living Cistanche (*Cistanche deserticola* Y. C. Ma, family Orobanchaceae) |
| Herba Cynomorii | Dried freshly stem of Songaria Cynomorium Herb (*Cynomorium songaricum* Rupr., family Cynomoriaceae) |
| Herba Dianthi | Whoe plant of pink Dianthus (*Dianthus superbus* L.; *Dianthus chinensis* L.) |
| Herba Epimedii | Dried aerial part of epimendium (*Epimedium brevicornum* Maxim., *Epimedium sagittatum* (Sieb. et Zucc.) Maxim., *Epimedium pubescens* Maxm., Epimedium wushanense T.S. Ying or *Epimedium koreanum* Nakai, family. Berberidaceae) |
| Herba Leonuri | Dried aerial part of Motherwort Herb (*Leonurus heterophyllus* Sweet, family Labiatae) |
| Herba Polygoni Avicularis | Whole plant of common knotgrass herb (*Polygonum avicutare* L., family Polygonaceae) |
| Medulla Junci | Common rush pith |
| Medulla Tetrapanacis | Ricepaper plant pith |
| Myrrha | Myrrh |
| Olibanum | Frankincense |
| Phaseolus Radiatus L | Mung bean |
| Polyporus Umbellatus | Underground tuberlike growths, (sclerotia) of agaric, an edible mushroom (*Polyporus umbrellatus*) |
| Radix Achyranthis Bidentatae | Two toothed Achyranthes Root (*Achyrantes bidentata* B1., family Amaranthaceae) |
| Radix Aconiti Kusnezoffii | Kusnezoff Monkshood Root (*Aconitum Kusnezoffii* Reichb., family Rununculaceae) |
| Radix Aconiti Praeparata | Monkshood Mother (Axial) Root (*Aconitum carmichaeli* Debx., family Ranunculaceae) |
| Radix Angelicae Dahuricae | Dahurian Angelica Root (*Angelica dahurica*, Fisch ex Hoffm., Benth. et Hook. f.; var. *formosana*, Boiss. Shan et Yuan; family Umbelliferae) |
| Radix Angelicae Pubescentis | Angelica root (*Angelica pubescens* Maxim. f. biserrata, Shan. et Yuan, family Umbelliferae) |
| Radix Angelicae Sinensis | Chinese Angelica Root |
| Radix Asparagi | Cochinchnese Asparagus Root |
| Radix Astragali seu Hedysari | Membranous Milkvetch Root/ Mongolian Milkvetch Root |

TABLE 1-continued

Herbal and Other Components and Sources

| Medicinal Name | Common Source Name (Botanical Source Name) |
|---|---|
| Radix Aucklandiae | Common Aucklandia Root (*Aucklandia lappa* Decne., family. Compositae) |
| Radix Bupleuri | Chinese Thorowax Root/Red Thorowax Root |
| Radix Clematidis | Root and rhizome of Chinese Clematis (*Clematis chinensis* Osbeck, *Clematis hexapetala* Pall. or *Clematis manshurica* Rupr., family Ranunculaceae) |
| Radix Codonopsis Pilosulae | Pilose Asiabell Root/Moderate Asiabell Root/Szechwon Tangshen Root |
| Radix Dipsaci | Dipsacus root, Teasel root (*Dipsacus asper* Wall.) |
| Radix et Rhizoma Rhei | Dried root and rhizome of Rhubard (*Rheum palmatum* L., *Rheum tanguticum* Maxim. ex Reg. Or *Rheum officinale* Baill, family Polygonaceae) |
| Radix Gentianae Macrophyllae | Large leaf Gentian Root (*Gentiana macrophylla* Pall., *Gentiana straminea* Maxim., *Gentiana crassicaulis* Duthie ex Burk. or *Gentiana dahurica* Fisch.; family Gentianaceae) |
| Radix Glycyrrhizae | Licorice root; Liquoric Root |
| Radix Linderae | Combined Spicebush Root |
| Radix Ophiopogonis | Dwarf Lilyturf Tuber (*Ophiopogon japonicus* Thunb., Ker-Gawl, family Liliaceae) |
| Radix Paeoniae Alba | White Paeony Root |
| Radix Paeoniae Rubra | Red Paeony Root |
| Radix Polygalae | Thinleaf Milkwort Root (*Polygala tenuifolia* Willd. or *Polygala sibirica* L., family Polygalaceae) |
| Radix Rehamanniae (crude) | Dried tuberous rehmannia root (*Rehmannia glutinosa* Gaertn Libosch or *Rehmannia glutinosa* Libosch F. hueichingensis, Chao et Schih; Hsiao) |
| Radix Rehmanniae Praeparata | Prepared rehmannia root (*Rehmannia glutinosa* Libosch) |
| Radix Scuttellariae | Baical skullcalp root (*Scutellaria baicalensis* Georgi, family Labiatae) |
| Radix Stephaniae Tetrandrae | Fourstamen Staphania Root (*Stephania tetrandria* S. Moore, family Menispermaceae) |
| Radix Trichosanthis | Mongolian Snakegourd Root (*Trichosanthes kirilowii* Maxim. or several species of the same genus, family Cucurbitaceae) |
| Ramulus Cinnamomi | Dried young stem of Cassia Twig (*Cinnamomum cassia* Presl, family Lauraceae) |
| Rhizoma Acori Graminei | Grassleaved Sweetflag Rhizome (*Acorus gramineus* Soland., family Araceae) |
| Rhizoma Alismatis | Stem tuber of Oriental Wateplantain (*Alismataci orientale* (Sam.) Juzep., family Alismataceae) |
| Rhizoma Anemarrhenae | Common anemarrhena Rhizome |
| Rhizoma Atractylodis | Large head Atractylodes Rhizome (*Atractylodes macrocephala* Roidz., family Compositae) |
| Rhizoma Belamcandae | Blackberrylily Rhizome (*Belamcanda chinensis* (L.) DC, family Iridaceae) |
| Rhizoma Cimicifugae | Large trifoliolious Bugbane Rhizome |
| Rhizoma Corydalis | Dried tuber of Yanhusuo (*Corydalis turtschaninovii* Bess., family Papaveraceae) |
| Rhizoma Dioscoreae | Rhizome of Chinese yam, Dioscorea; (*Dioscrorea opposita* Thunb.) |

TABLE 1-continued

Herbal and Other Components and Sources

| Medicinal Name | Common Source Name (Botanical Source Name) |
|---|---|
| Rhizoma Dioscoreae Hypoglaucae | Tokoro; Hypoglaucous Collett Yam Rhizome (*Dioscorea hypoglauca* Palibin and several other species of the same genus, family Dioscoreaceae, or some species of Smilax; family Liliaceae) |
| Rhizoma Ligustici Chuanxiong | Dried rhizome and root of Chinese Lovage (*Ligusticum sinense* Oliv. or *Ligusticum jeholense* Nakai et Kitag; family. Umbelliferae) |
| Rhizoma seu Radix Nototerygii | Notopterygium root and/or rhizome (*Notopterygium incisum* Ting ex H.T. Chang; or *N. forbesii* Boiss, family Umbelliferae) |
| Rhizoma Zingiberis Recens | Fresh Ginger Rhizome (*Zingiber officinale* (Willd.) Rosc., family. Zingiberaceae) |
| Semen Biotae | Biota seed, Arborvitae seed (*Biota orientalis* (L.) Endl.) |
| Semen Coicis | Coix seed (*Cois lacryma-jobi* L. var. *ma-yuen* (Roman.) Stapf) |
| Semen Cuscutae | Dadder seed, Cuscuta seed (*Cuscuta chinensis* Lam.; *Cuscuta japonica* Choisy) |
| Semen Dolichoris Album | White hyacinth bean |
| Semen Euryales | Gordon Euryale Seed |
| Semen Pharbitidis | Pharbitis Seed (*Pharbitis nil* (L.) Choisy or *Pharbitis pupurea* (L.) Voigt, family Convolvulaceae) |
| Semen Plantaginis | Dried, ripe plantain seed (*Plantago asiatica* L. and other species of the same genus, family Plantaginaceae) |
| Semen Persicae | Persica seed, Peach see (*Prunus persica* (L.) Batch; *Prunus davidiana* (Carr.) Franch.) |
| Spica Prunellae | Prunella spike; Selfheal spike (*Prunella vulgaris* L., family Labiatae) |
| Stigma Maydis | Corn style and stigma; corn silk (*Zea mays* L., family Gramineae) |

In a preferred embodiment, the herbal composition includes at least the first 44 components listed in Table 2, below, which are selected from Table 1. More preferably, the extract also includes component 45 in Table 2, namely, *Ganoderma Lucidum*.

TABLE 2

Components of a Preferred Embodiment

| Nr | Component | Amount (gm) | Ratio to Least Abundant | Percent (w/w) |
|---|---|---|---|---|
| 1 | Radix Asparagi | 640 | 6 | 2.34% |
| 2 | Radix Angelicae Pubescentis | 640 | 6 | 2.34% |
| 3 | Radix Trichosanthis | 860 | 9 | 3.14% |
| 4 | Radix Scuttellariae | 384 | 4 | 1.40% |
| 5 | Radix Angelicae Sinensis | 100 | 1 | 0.37% |
| 6 | Radix Dipsaci | 100 | 1 | 0.37% |
| 7 | Cortex Eucommiae | 100 | 1 | 0.37% |
| 8 | Medulla Junci | 100 | 1 | 0.37% |
| 9 | Rhizoma Anemarrhenae | 384 | 4 | 1.40% |
| 10 | Caulis Akebiae | 768 | 8 | 2.81% |
| 11 | Herba Dianthi | 768 | 8 | 2.81% |
| 12 | Semen Plantaginis | 640 | 6 | 2.34% |
| 13 | Cortex Phellodendri (fried) | 768 | 8 | 2.81% |
| 14 | Radix et Rhizoma Rhei | 384 | 4 | 1.40% |
| 15 | Rhizoma seu Radix Notopterygii | 100 | 1 | 0.37% |
| 16 | Olibanum | 100 | 1 | 0.37% |
| 17 | Fructus Gardeniae | 668 | 7 | 2.44% |

TABLE 2-continued

Components of a Preferred Embodiment

| Nr | Component | Amount (gm) | Ratio to Least Abundant | Percent (w/w) |
|---|---|---|---|---|
| 18 | Radix Astragali seu Hedysari | 1500 | 15 | 5.48% |
| 19 | Rhizoma Cimicifugae | 384 | 4 | 1.40% |
| 20 | Radix Bupleuri | 384 | 4 | 1.40% |
| 21 | Myrrha | 100 | 1 | 0.37% |
| 22 | Gypsum Fibrosun | 1820 | 18 | 6.65% |
| 23 | Radix Rehamanniae (crude) | 1500 | 15 | 5.48% |
| 24 | Folium Pyrrosiae | 860 | 9 | 3.14% |
| 25 | Rhizoma Acori Graminei | 640 | 6 | 2.34% |
| 26 | Rhizoma Dioscoreae Hypoglaucae | 640 | 6 | 2.34% |
| 27 | Radix Linderae | 640 | 6 | 2.34% |
| 28 | Herba Cistanche | 100 | 1 | 0.37% |
| 29 | Radix Paeoniae Rubra | 640 | 6 | 2.34% |
| 30 | Rhizoma Dioscoreae | 860 | 9 | 3.14% |
| 31 | Semen Euryales | 640 | 6 | 2.34% |
| 32 | Cortex Mouton | 100 | 1 | 0.37% |
| 33 | Polyporus Umbellatus | 640 | 6 | 2.34% |
| 34 | Radix Rehmanniae Praeparata | 100 | 1 | 0.37% |
| 35 | Medulla Tetrapanacis | 640 | 6 | 2.34% |
| 36 | Semen Coicis | 768 | 8 | 2.81% |
| 37 | Fructus Horedi Germinatus (Poria) | 860 | 9 | 3.14% |
| 38 | Radix Aconiti Praeparata | 640 | 6 | 2.34% |
| 39 | Rhizoma Alismatis | 640 | 6 | 2.34% |
| 40 | Cortex Cinnamomi | 320 | 3 | 1.17% |
| 41 | Herba Asari | 384 | 4 | 1.40% |
| 42 | Radix Glycyrrhizae | 320 | 3 | 1.17% |
| 43 | Stigma Maydis | 1820 | 18 | 6.65% |
| 44 | Phaseolus Radiatus L | 3100 | 31 | 11.33% |
| 45 | Ganoderma Lucidum | 96 | 1 | 0.35% |
| Total | | 28,640 | | 100.00% |

The exact proportion of the Chinese herbs and other components in the composition will depend on the concentration of the active ingredients found naturally in each component. Using the guidance provided herein and a basic knowledge of drug preparation and pharmacology, one skilled in the art could easily adjust the proportions of the separate components of the composition so as to obtain a composition which has the therapeutic effects discussed and shown in the examples herein. The discussion below regarding proportions of ingredients in the composition are provided as examples only and in no way limit the scope of the present invention from including any novel combination of the disclosed herbal and non-herbal components which have the intended effect of relieving symptoms associated with prostate conditions, as discussed herein. In particular, the individual component amounts of the particularly preferred composition of the invention described in Table 2 may be varied, for instance, cut in half or increased by twofold, depending on the quality of the individual components.

In this particularly preferred embodiment described in Table 2, the herbal composition of the invention comprises an extract made from each of the 45 components in Table 2, in the relative amounts (w/w ratios of crude preparations) shown therein, compared to the least abundant components. The yield of dry powdered extract mixture prepared from the relative amounts of crude dried herbal components shown in Table 2 is about 5 to 6%. For instance, one exemplary preparation begun with 10 Kg of dried herbs and other components as specified in Table 2, prepared as described in Example 1, yielded 548 gm of dried powder extract (about 5.5% yield).

Recommended human daily dosage of the above particularly preferred embodiment is preferably in the range of about 12 to 24 gm once or twice per day, more preferably 12–18 gm twice per day, for a minimum time period of one week to about 30 days. Continuance of this regimen of the invention, along with a proper balanced diet results in continued amelioration of prostate conditions including prostatitis, benign prostate hyperplasia, and prostate malignancy. Further, the regimen is suitable as preparation for surgical treatment, to help solid tumors to become isolated and encapsulated with respect to surrounding tissue so that they can more easily be removed. The regimen is also suitable for periodic use in aging men free of symptoms of prostatitis and benign prostate hypertrophy (BHP), to prevent occurrence of such symptoms which include pelvic pain (in the groin, testicles, and penis), and/or voiding symptoms including getting up at night to void (nocturia), frequency and urgency of urination, incomplete voiding, decreased force of the urinary stream, intermittence of the stream and a need to push or strain to void, and impotence or erection difficulties and male infertility associated with prostatitis. In any event it is important to emphasize that the regimen must include an adequate diet in other respects to ensure that the subject can mount the requisite disease-fighting response(s).

The herbal compositions and extracts thereof of the invention are preferably administered orally and can be prepared as foods of acceptable flavor and texture by methods generally known in the art. The herbal compositions and extracts also can be used in the form of a dietary supplement or as a medicinal preparation, for example, in solid, semisolid or liquid form which contains the composition of the present invention, as an extract or as a purified active ingredient, either alone in admixture with an organic or inorganic carrier or excipient suitable for external, enteral or parenteral applications. The active ingredients may be compounded, for example, with the usual non-toxic pharmaceutically acceptable carriers for tablets, pellets, capsules, suppositories, solutions, emulsions, suspensions, and any other form suitable for use. Formulations of the present invention encompass those which include carriers such as talc, water, glucose, lactose, gum acacia, gelatin, mannitol, starch paste, magnesium trisilicate, corn starch, keratin, colloidal silica, potato starch, urea and other carriers suitable for use in manufacturing preparations, in solid, semisolid or liquid form. In addition auxiliary, stabilizing, thickening and coloring agents and perfumes may be used.

For preparing solid compositions such as tablets or capsules, the extract or principal active ingredients are mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of a composition of the present invention, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as tablets, pills and capsules. This solid preformulation composition is then subdivided into unit dosage forms known in the art, preferably in capsules. Tablets or pills of the novel composition can be coated or otherwise compounded to provide a dosage form affording the advantage of prolonged action. For example, the tablet or pill can comprise an inner dosage an outer component, the latter being in the form of an envelope over the former.

Liquid forms, in which novel compositions of the present invention may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin. Liquid preparations for oral administration may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners. For buccal administration, the composition may take the form of tablets or lozenges formulated in conventional manners. Compositions of the invention also my be formulated and administered via conventional suppository technologies.

The extracts or active compounds thereof may be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

EXAMPLE 1

Reduction of Prostate Tumor Progression in Scid Mice

Materials
Extract:
The extract used in this study was prepared by lyophilization of an aqueous extract ("tea") prepared from the 45 medicinal components listed in Table 2, above, by sequential extraction and/or solubilization of each of the component materials with a single aliquot of hot water at or near the boiling point (typically 100 cc water per 100 gm of total starting material). After extraction of the last component, the solution was allowed to cool to room temperature and filtered through a paper filter (e.g., Whatman #1) to remove insoluble materials.

Animal Diets:
Control diet Purina 5001 rat chow (Purina TestDiet, Richmond, Ind.)
Test Diet #1 Purina 5001 rat chow containing 240 mg/kg herbal extract
Test Diet #2 Purina 5001 rat chow containing 480 mg/kg herbal extract
Test Diet #3 Purina 5001 rat chow containing 720 mg/kg herbal extract
All test diets were prepared by Purina TestDiet, Richmond, Ind. and supplied sterile (gamma irradiation) by Purina. Daily dose was derived from human consumption levels proportioned to mouse weight. This quantity was then added to the diet at an average daily consumption volume for mice.

Experimental Design
A. Animals:

| | |
|---|---|
| Species: | Mouse |
| Strain: | Severe combined immuno-deficient (Scid) Mice |
| Source: | University of Arizona, Arizona Cancer Center, Tucson, AZ 85724 |
| Weight: | 20–25 grams |
| Number/Sex: | 32/male or female |

B. Husbandry:
Housing:
The animals were housed two per cage in micro-isolator cages on wood shavings.
Food:
Each animal received Tech-Lad 4% Mouse/Rat Diet® ad libitum. The feed is analyzed by the manufacturer for concentrations of specified heavy metals, aflatoxin, chlorinated hydrocarbons, PCBs, organophosphates, and specified nutrients. After tumors cells were injected into the mice, test animals were fed the herbal extract diet incorporated into Purina 5001 base diet and the control group was fed Purina 5001 diet without the extract.
Water:
Tap water was available ad libitum. The water was routinely analyzed on a retrospective basis for specified microorganisms, pesticides, heavy metals, alkalinity and halogens.
Environment:
The rooms were controlled at a temperature of 74° F.±10° F., and at a humidity of 50%±20% in accordance with the NIH Guide for the Care and Use of Laboratory Animals.
C. Procedures:
General:
Groups of SCID mice were injected subcutaneously with cells ($1 \times 10^5$ cells/mouse) derived from the prostate carcinoma cell line, DU145 (Carter et al., Proc. Natl. Acad. Sci. USA, 93, 749–753 (1996). All 4 groups were injected with tumor cells and immediately placed on different feeds according to group designation. The 4 groups were as follows: 1) control group maintained on regular Purina 5001 rat diet; 2) test group placed on Purina 5001 rat diet containing a dose of 240 mg/kg herbal extract; 3) test group placed on Purina 5001 rat diet containing a dose of 480 mg/kg herbal extract, 4) placed on Purina 5001 rat diet containing a dose of 720 mg/kg herbal extract. The feed was provided ad libitum.

Tumor size was quantified 3 times a week using a caliper and recorded. Mice were sacrificed at 5–6 wk and tumors harvested and processed for histological evaluation. Mice were anesthetized, tumors were exposed, gross photographs were taken and samples were explanted. The samples were placed in Histochoice® fixative and processed for light microscopy (SOP A14-006). The samples were sectioned, placed on slides and stained with H&E (SOP A14-003a). In addition, each sample will be immunohistochemically stained with GS-1 (SOP Al 3-004) and Proliferating Cell Nuclear Antigen (PCNA) to determine cell proliferation rate.

Experiment #1
30 mice were injected with $7 \times 10^5$ DU145 tumor cells. Mice were divided into groups and immediately placed on Purina 5001 rodent diet ad libitum, containing herbal extract as follows:
Group 1: 0.024% (w/w)
Group 2: 0.048% (w/w)

Group 3: 0.072% (w/w)
Group 4: Control, no extract

Once tumor was established, tumors were measured and recorded 3 times a week. At 6 wks all tumors were explanted. Gross photographic images were taken, and all tumors were measured and weighed. Tumors were divided as follows: ⅔ to Histochoice® fixative and ⅓ to freeze with Isopentane in liquid nitrogen.

Results:

FIG. 1 shows the reduction in weekly average tumor volume of mice injected with human prostate (DU145) tumor cells in three groups fed differing amounts of herbal extract, compared to the Control group, during the course of a six-week study. Mean tumor volume in the control animals reached a peak between about 0.35 and 0.40 $cm^3$ between about 4 and 5 weeks after inoculation with tumor cells. Each tested dose of herbal extract reduced the mean tumor volume in a dose-dependent manner. Thus, mean tumor volume of animals given feed with 0.024% (w/w) herbal extract peaked at about 0.20 $cm^3$, whereas those with 0.048% (w/w) herbal extract peaked at about 0.15 $cm^3$, and those with 0.072% (w/w) herbal extract reached a highest level of about 0.09 $cm^3$ at the end of the study, after the tumor volume of the other groups had peaked.

Figure 2:
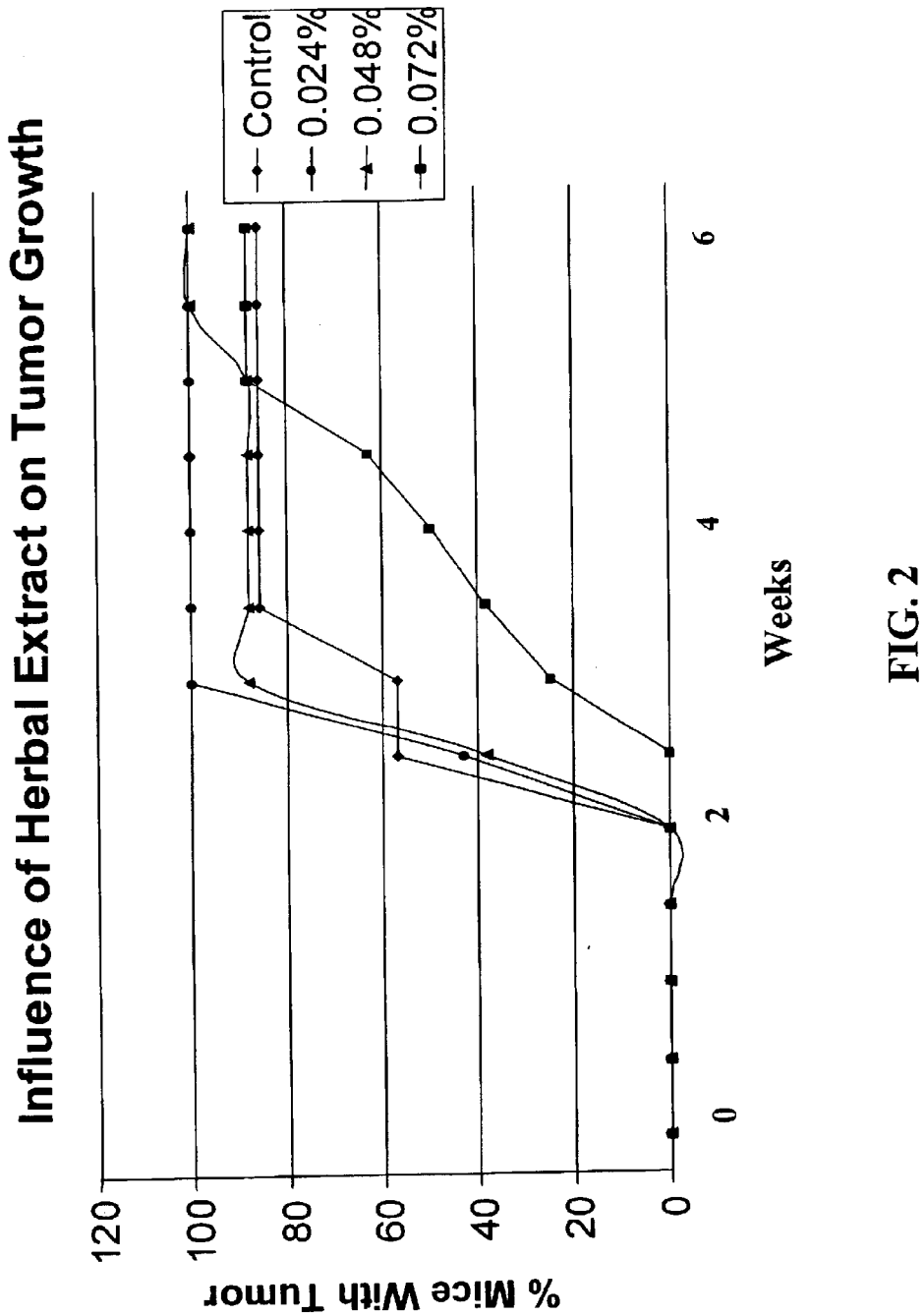
FIG. 2 shows the influence of herbal extract on tumor incidence after inoculation of mice with human prostate tumor cells.

FIG. 2 shows the influence of herbal extraction tumor incidence after inoculation of mice with human prostate tumor cells. The percentage of mice with palpable tumors in the control group reached a plateau at about 90% between about 2 and 3 weeks after inoculation with tumor cells. Only the highest tested dose of herbal extract (0.072% (w/w)) delayed the incidence of palpable tumor, with 100% incidence occurring only at 6 weeks.

Figure 3:
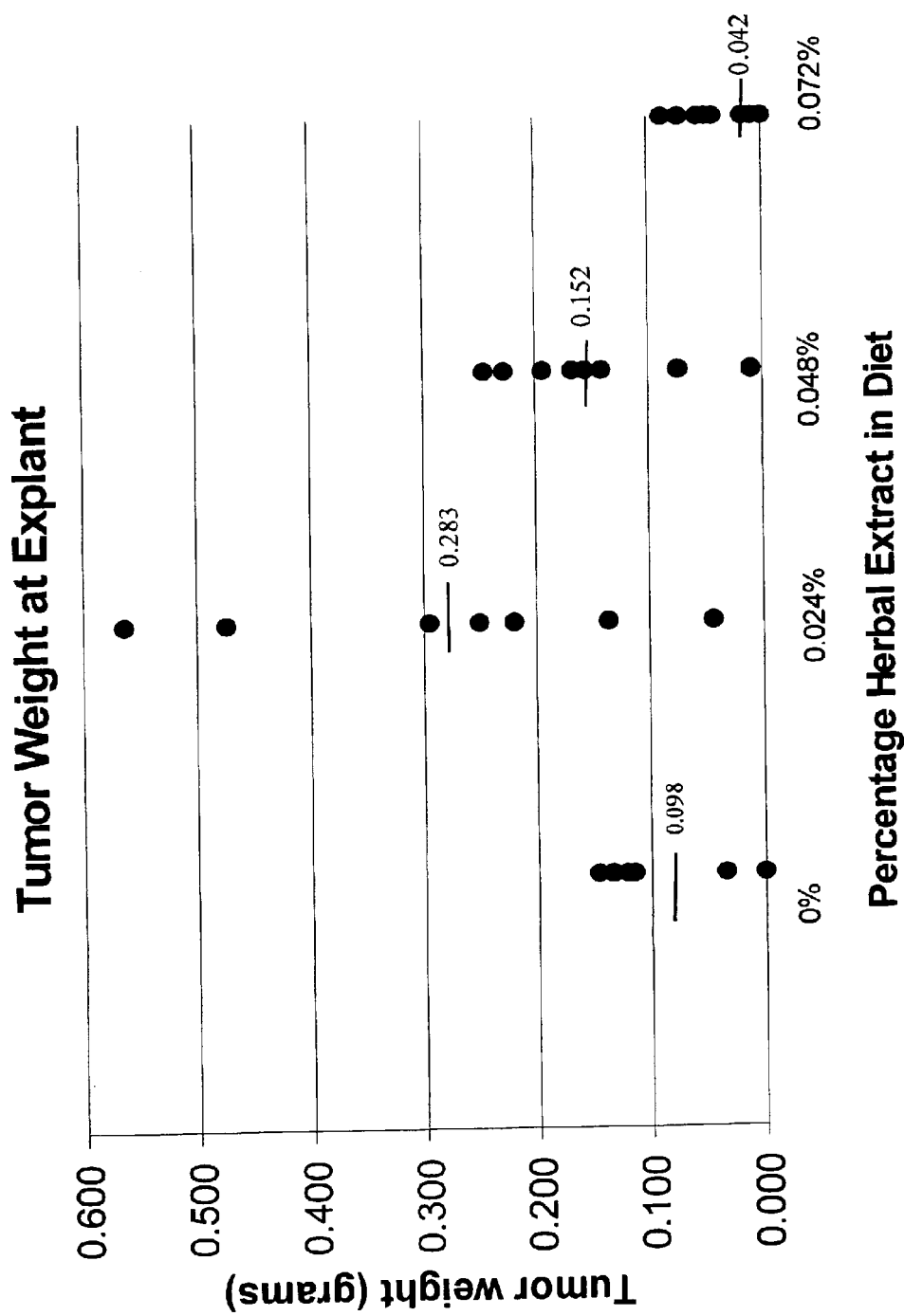
FIG. 3 shows the influence of herbal extract on the distribution of explanted tumor weights in each treated group.
Figure 4:
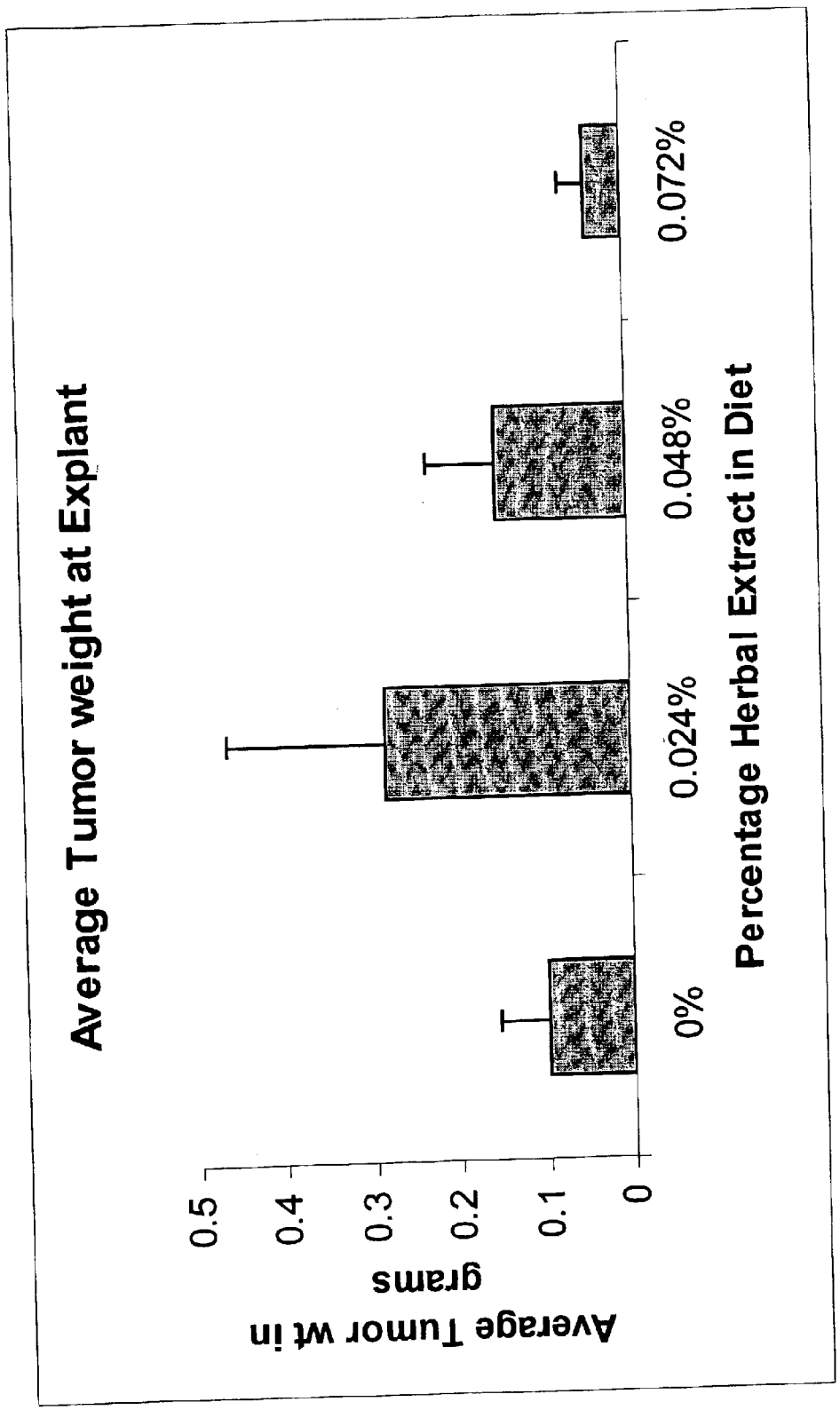
FIG. 4 displays the mean values of explanted tumor weights in each treated group, with scatter ranges.

FIG. 3 and FIG. 4 shows the influence of herbal extract on tumor weight at explant (i.e., the end of the study, 6 weeks). FIG. 3 shows the distribution of explanted tumor weights in each group, whereas FIG. 4 displays the mean values with scatter ranges. Again, only the highest tested dose of herbal extract (0.072% (w/w)) showed a significant reduction in explanted tumor weight, by a factor of about two, from a mean of about 0.098 grams in the control group, to a mean of about 0.042 grams.

Figure 5:
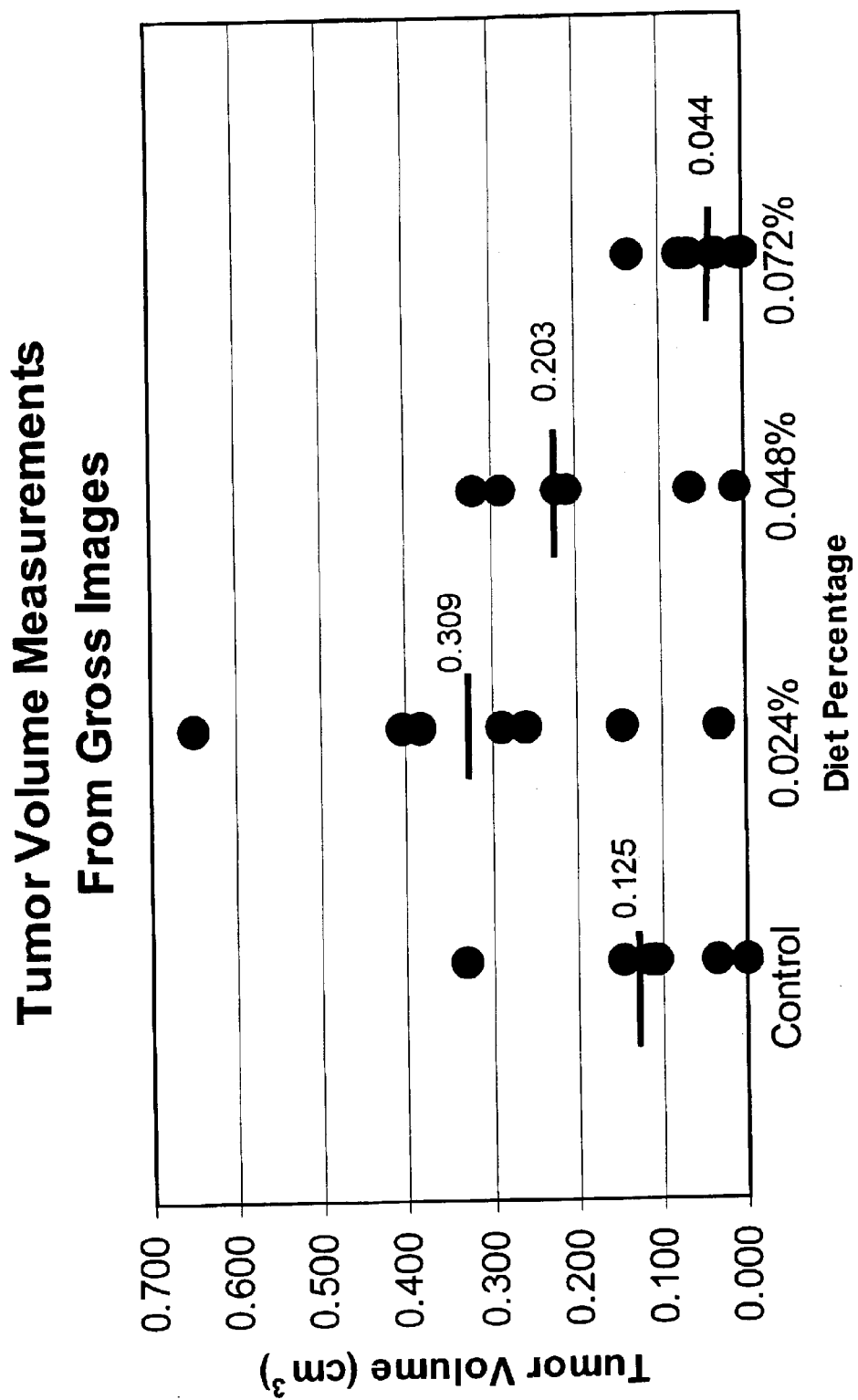
FIG. 5 shows the influence of herbal extract on tumor volume at explant, measured from gross photo images.

FIG. 5 shows the influence of herbal extract on tumor volume at explant, measured from gross photo images. Tumor volumes generally were proportional to tumor weights and, again, only the highest tested dose of herbal extract (0.072% (w/w)) showed a significant reduction in explanted tumor volume.

EXAMPLE 2

Experiment #2
Evaluation of Larger Tumor Inoculum and a Second Batch of Herbal Extract 30 mice were injected with 1×10⁶ DU145 tumor cells, as in Example 1 (where 7×10⁵ cells were used), and were divided into groups and immediately placed on Purina 5001 rodent diet ad libitum, containing herbal extract in a broader range of doses, as follows:

Group 1: 0.0072% (w/w) ("old" extract #1=same batch as Example 1)
Group 2: 0.0072% (w/w) ("new" extract batch #2, made as in Example 1)
Group 3: 0.024% (w/w) ("old" extract #1=same batch as Example 1)
Group 3: 0.024% (w/w) ("old" extract #1=same batch as Example 1)
Group 4: 0.024% (w/w) ("new" extract batch #2, made as in Example 1)
Group 5: 0.048% (w/w) ("old" extract #1=same batch as Example 1)
Group 6: 0.048% (w/w) ("new" extract batch #2, made as in Example 1)
Group 7: 0.072% (w/w) ("old" extract #1=same batch as Example 1)
Group 8: 0.072% (w/w) ("new" extract batch #2, made as in Example 1)
Group 9: 0.72% (w/w) ("old" extract #1=same batch as Example 1)
Group 10: 0.72% (w/w) ("new" extract batch #2, made as in Example 1)
Group 11: Control, no extract Tumors were measured and recorded 3 times a week and at 6 weeks tumors were explanted and processed as in Example 1, above.

Figure 6:
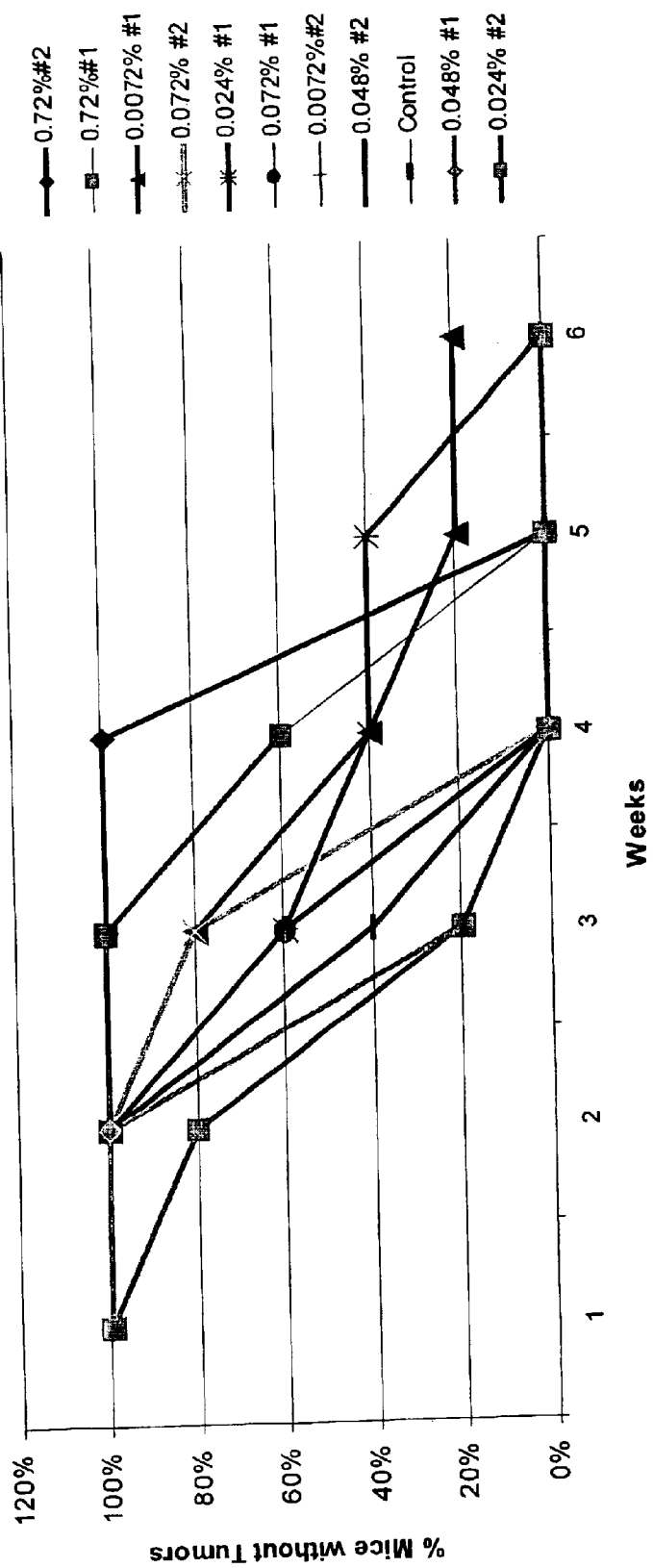
FIG. 6 shows the influence of different batches and doses of herbal extract on tumor incidence.

Results:

FIG. 6 shows the influence of different batches and doses of herbal extract on tumor incidence. The percentage of mice without palpable tumors in the control group began to fall after 2 weeks and reached 0% at about 4 weeks after inoculation with tumor cells. The highest tested dose of herbal extract (0.72% (w/w)) from both batches (#1 and #2) significantly delayed the onset of palpable tumors by about 1–2 weeks, with 0% tumor-free mice occurring only at 5 weeks.

Figure 7:
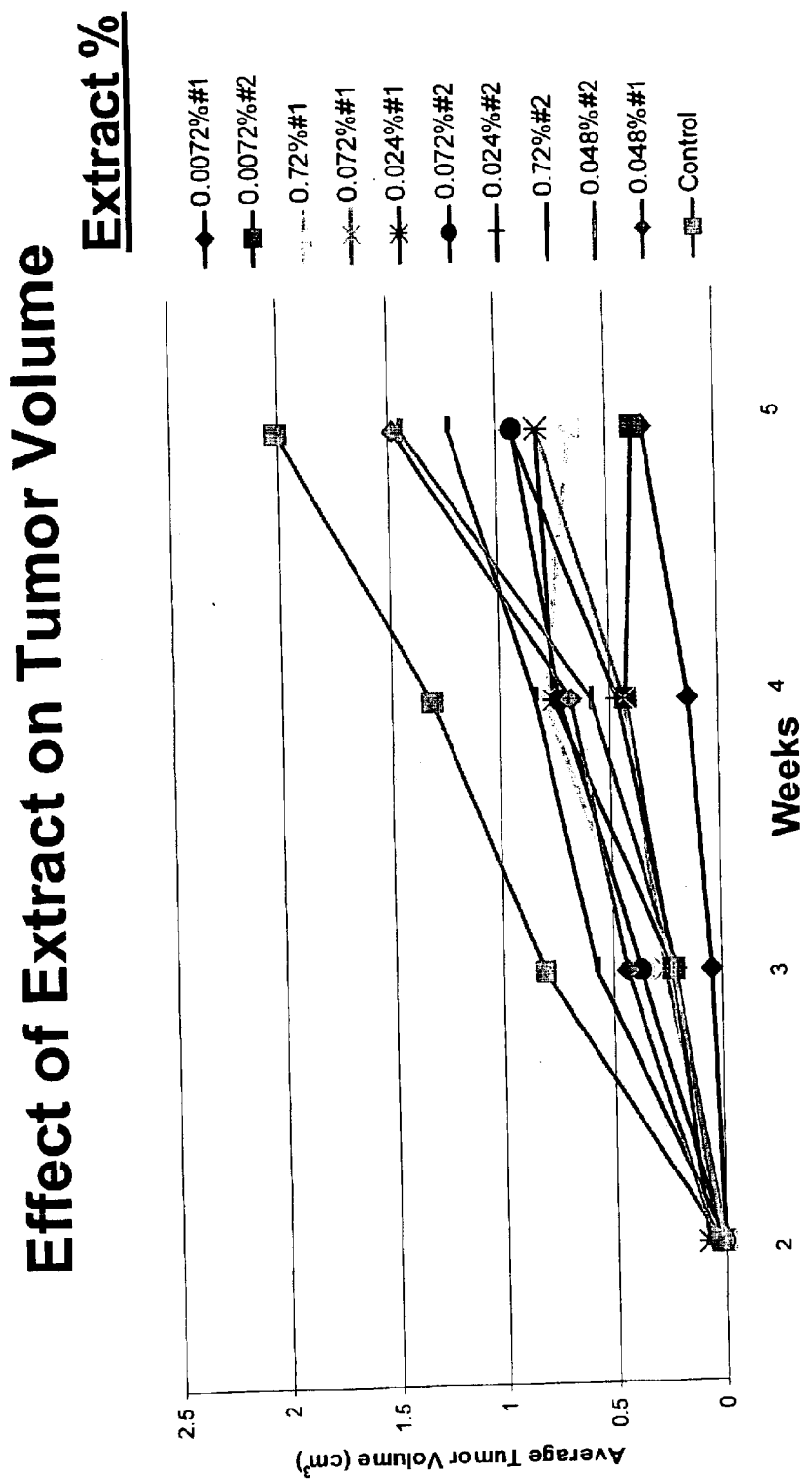
FIG. 7 shows the weekly average tumor volumes of mice in the various groups fed different batches and doses of herbal extract and the Control group
Figure 8:
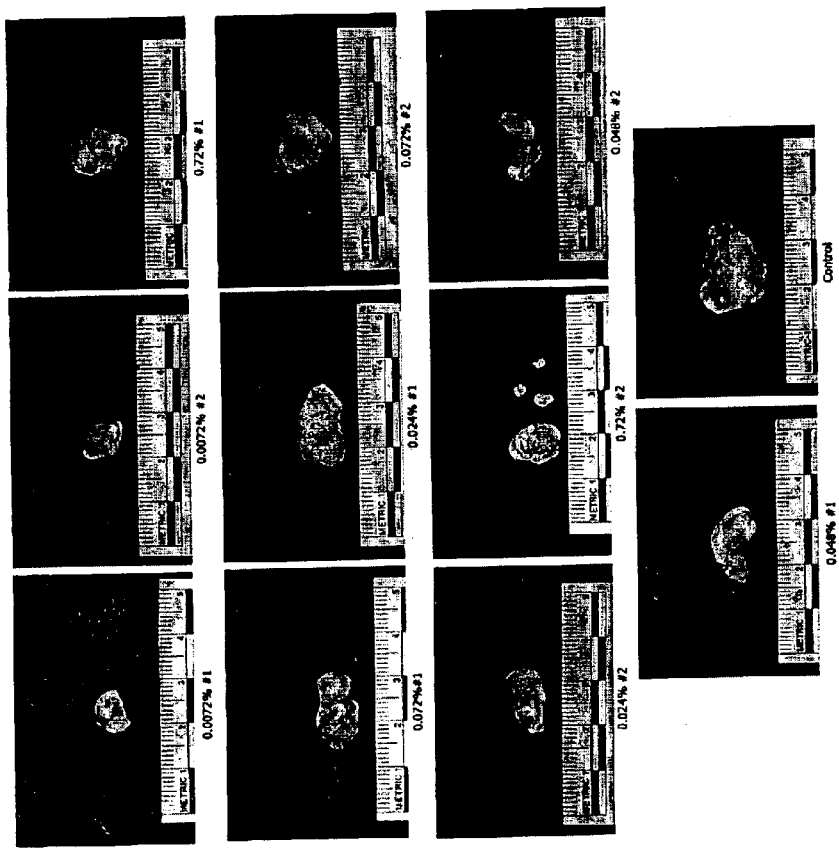
FIG. 8 shows photographs of selected explanted tumors visually illustrating the reduction of tumor size in animals treated with the herbal extract.

FIG. 7 shows the weekly average tumor volume of mice in the various groups fed different batches and doses of herbal extract and the Control group during the course of the study. Mean tumor volume in the control animals reached about 2.0 $cm^3$ at 5 weeks after inoculation with tumor cells. Each tested dose of herbal extract reduced the mean tumor volume, but not in a strictly dose-dependent manner. Thus, mean tumor volume of animals given feed with 0.72% (w/w) herbal extract was about 0.4 $cm^3$ at 5 weeks, using either the old (#1) or new (#2) batches, while the mean volume at 5 weeks for each of the other doses was in a range of about 0.8 to 1.5 $cm^3$. FIG. 8 shows photographs of selected explanted tumors visually illustrating the reduction of tumor size in animals treated with the herbal extract.

Figure 9:
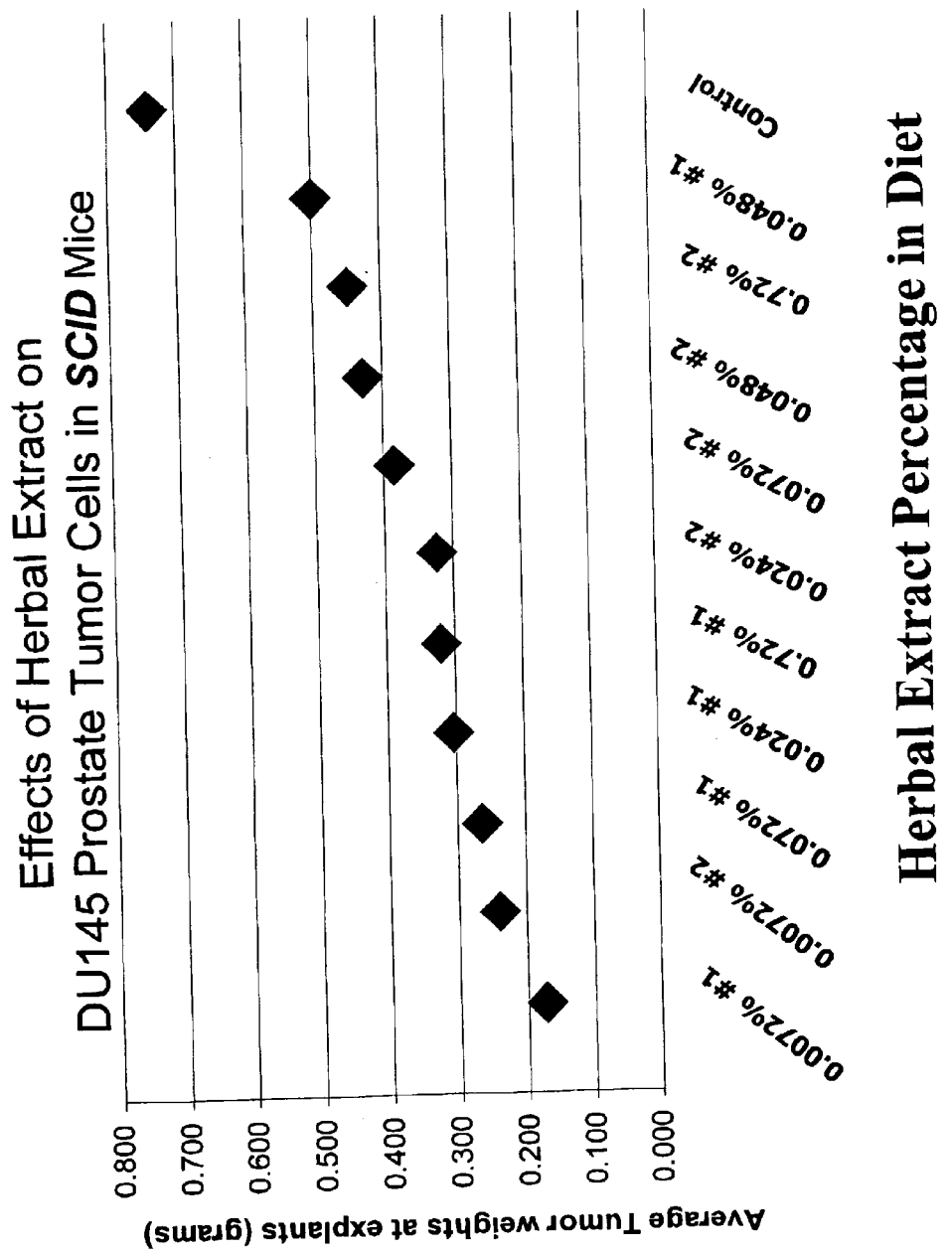
FIG. 9 shows the influence of herbal extract on mean tumor weight at explant for various batches and doses of extract.

FIG. 9 shows the influence of herbal extract on mean tumor weight at explant (i.e., the end of the study, 6 weeks), showing that all tested doses of both batches of herbal extract significantly reduced explanted tumor weight, by about 30–70%, from about 750 gm to about 200–500 gm.

Figure 10:
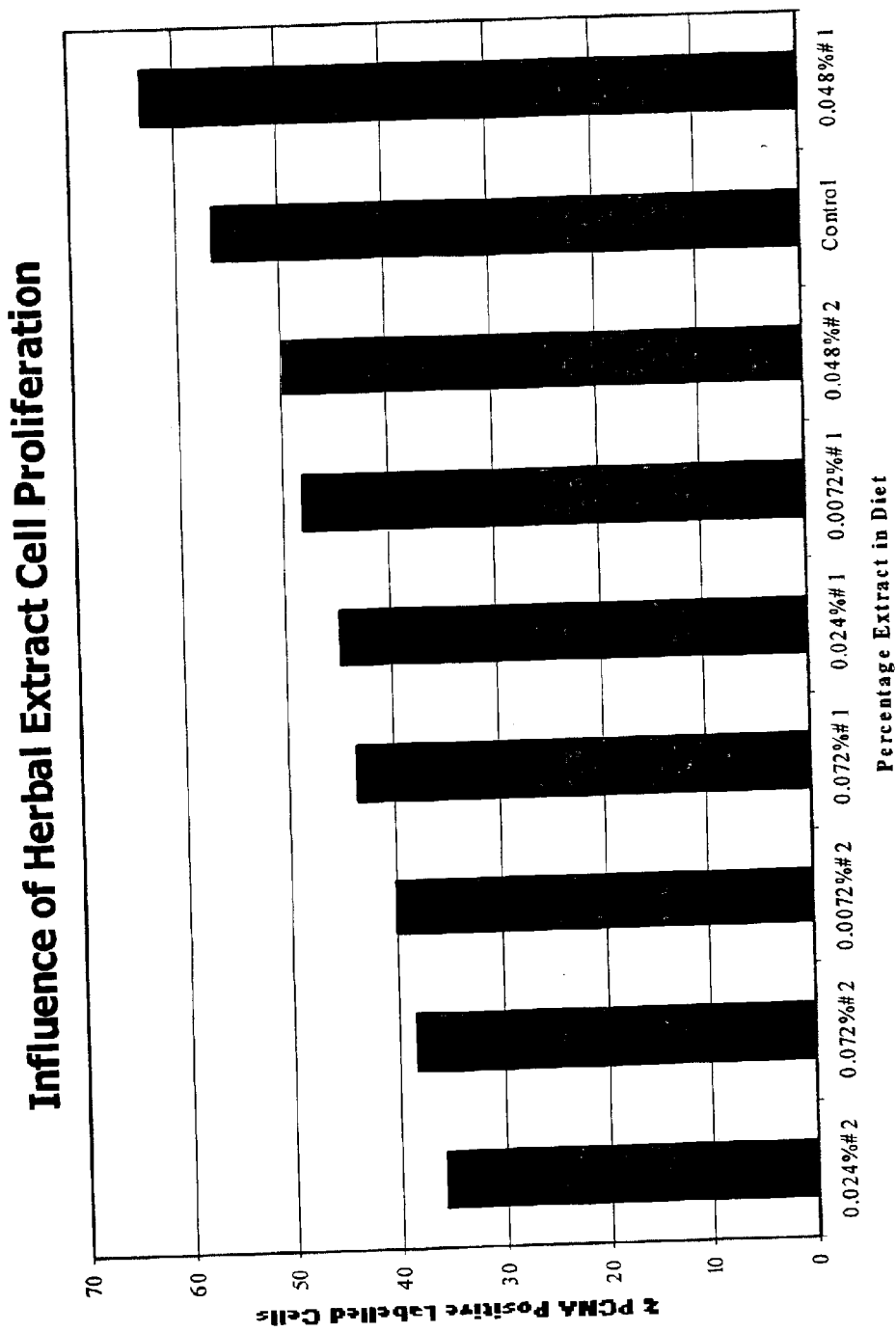
FIG. 10 graphically shows the influence of herbal extract on tumor cell proliferation as measured by Proliferating Cell Nuclear Antigen (PCNA) as an indicator of cell proliferation rate.
Figure 11:
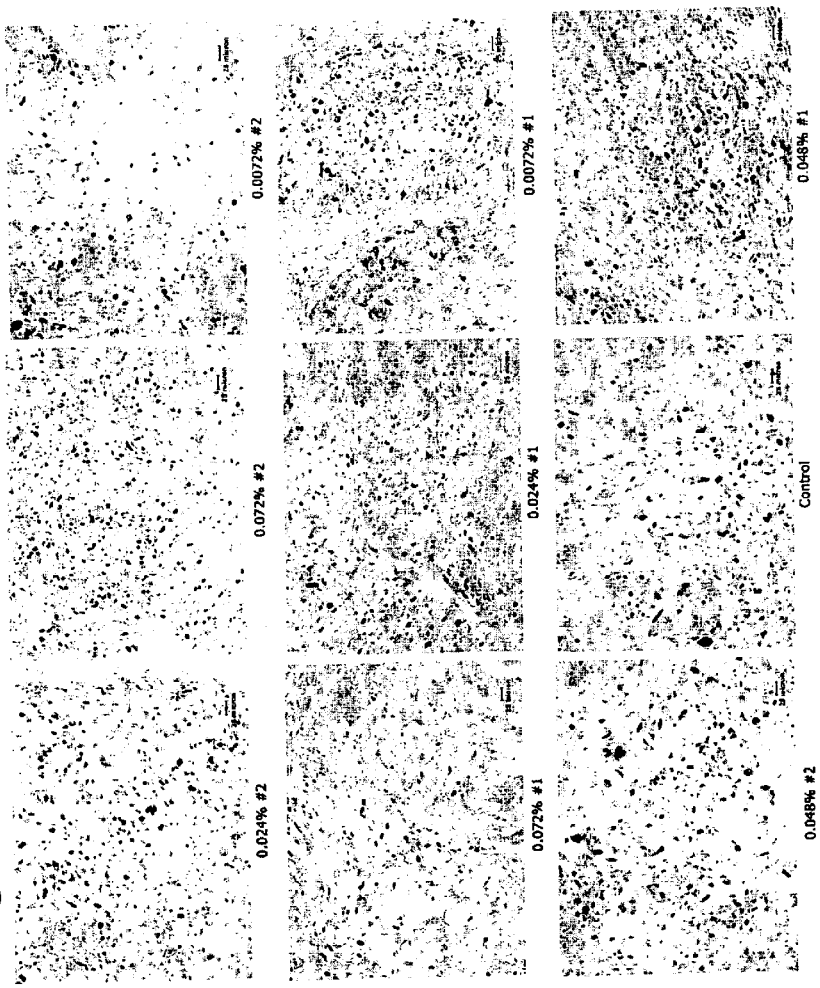
FIG. 11 shows photographs of selected tumor sections stained for PCNA, illustrating typical visual fields for various herbal extract doses.

FIGS. 10 and 11 show the influence of herbal extract on tumor cell proliferation, as measured by Proliferating Cell Nuclear Antigen (PCNA) as an indicator of cell proliferation rate. As shown graphically in FIG. 10, generally, doses for which PCNA was determined showed reductions in cell proliferation rate compared to the control, except for one group (0.048% of Extract #1; tumors from animals at the highest dose were not tested for PCNA), but these reductions did not show a clear dose-dependent pattern. FIG. 11 shows photographs of selected tumor sections stained for PCNA, illustrating typical visual fields for various herbal extract doses.

EXAMPLE 3

Experiment #3
Retesting of Two Batches and Dosages 30 mice were injected with 1×10⁶ DU145 tumor cells, as in Example 1, and were divided into groups and immediately placed on Purina 5001 rodent diet ad libitum, containing herbal extract in a high or low dose, as follows:

Group 1: 0.072% (w/w) ("old" extract #1=same batch as Example 1)

Group 2: 0.072% (w/w) ("new" extract batch #2, made as in Example 1)

Group 3: 0.72% (w/w) ("old" extract #1=same batch as Example 1)

Group 4: 0.72% (w/w) ("new" extract batch #2, made as in Example 1)

Group 5: Control, no extract

Tumors were measured and recorded 3 times a week and at 6 weeks tumors were explanted and processed as in Example 1, above.

Figure 12:
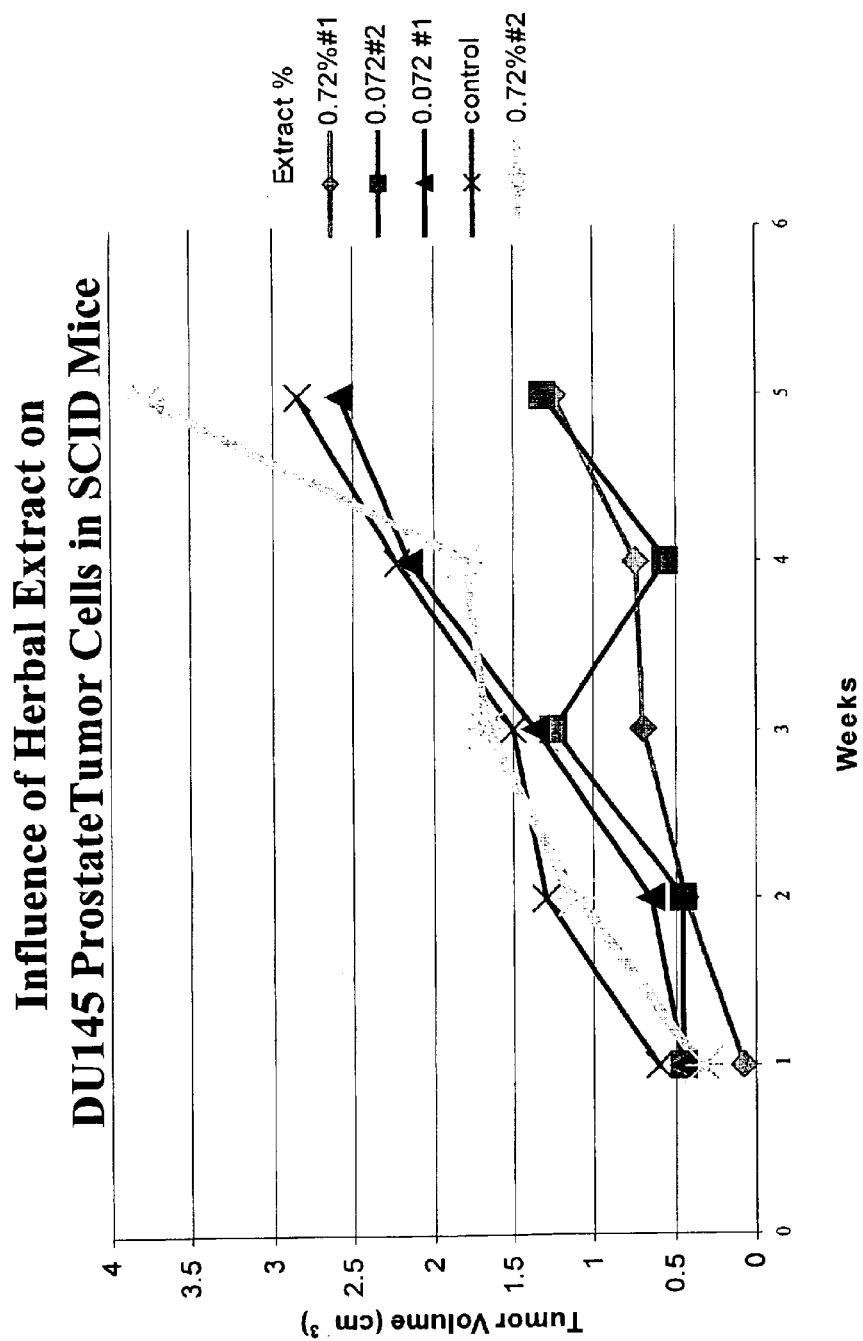
FIG. 12 shows the influence of herbal extract on the weekly average tumor volume of mice in various groups fed different batches and doses of herbal extract and the Control group.
Figure 13:
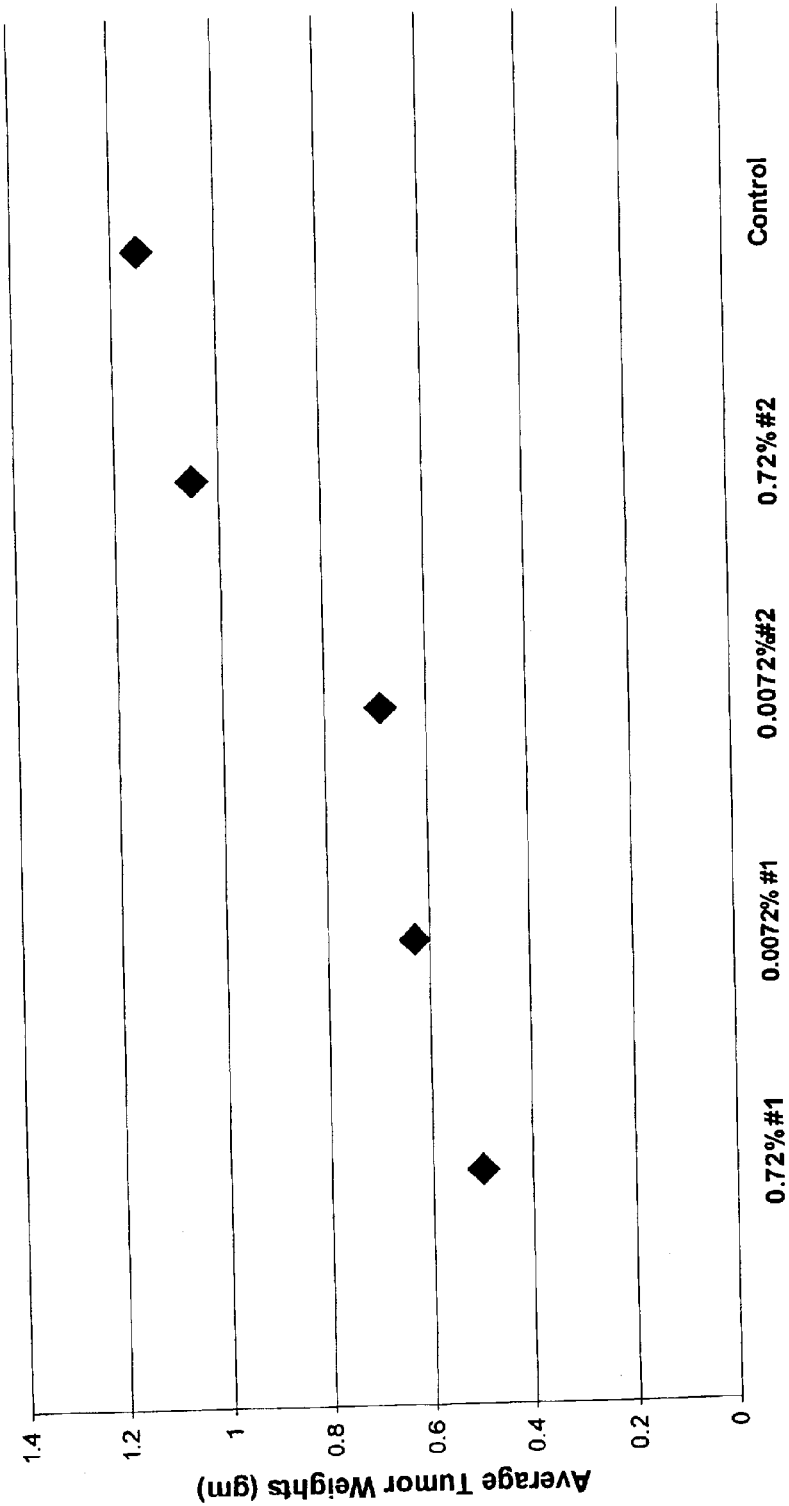
FIG. 13 shows the influence of herbal extract on mean tumor weight at explant for the same mice used in FIG. 12.
Figure 14:
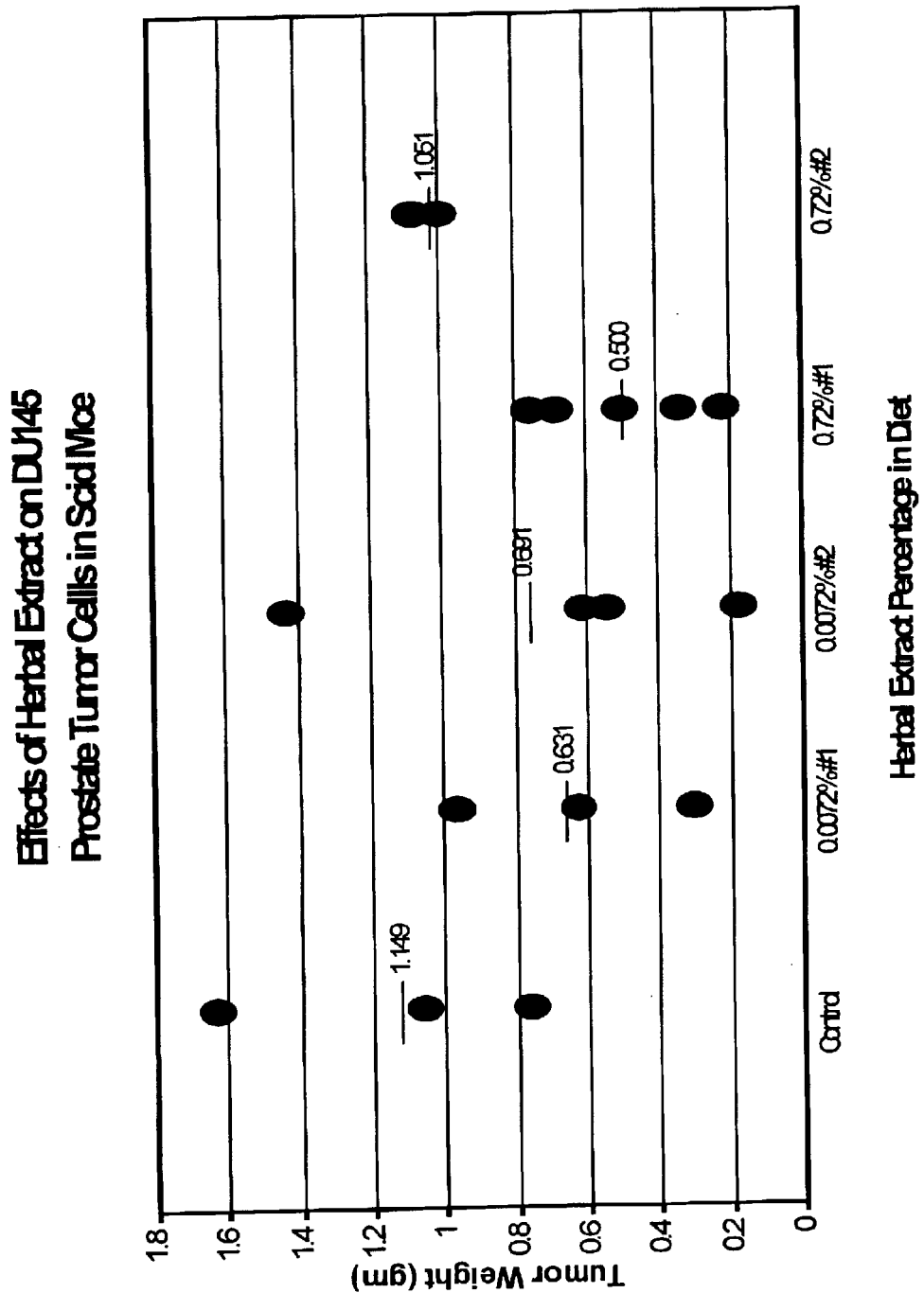
FIG. 14 shows individual tumor weights of mice included in the averages shown in FIG. 13.

Results:

FIG. 12 shows the influence of herbal extract on the weekly average tumor volume of mice in the various groups fed herbal extract and the Control group during the course of the study. Mean tumor volume in the control animals reached about 2.8 cm$^3$ at 5 weeks after inoculation with tumor cells. Only the 0.72% (w/w) dose rate of herbal extract #1 and the 0.072 % (w/w) dose rate of herbal extract #2 reduced the mean tumor volume compared to control animals receiving no extract, to about the same level. Thus, mean tumor volumes of animals given feed with 0.72% (w/w) herbal extract #1 or 0.072% (w/w) herbal extract #2 were each about 1.3 cm$^3$ at 5 weeks, compared to about 2.8 cm$^3$ for control animals (FIG. 12). FIG. 13 shows the influence of herbal extract on mean tumor weight at explant (i.e., the end of the study, 6 weeks), showing that at that time all tested doses of both batches of herbal extract (except 0.72% (w/w) herbal extract #2) significantly reduced explanted tumor weight, by about 40–56%, from about 1.149 gm to about 0.691–0.500 gm. Individual tumor weights of mice included in these averages are shown in FIG. 14. The lower effectiveness, in terms of reducing tumor volume and weight, of 0.72% (w/w) herbal extract #2 compared to lower doses of the same extract is not understood but was also observed in Example 2 (see FIGS. 7 and 9).

Figure 15:
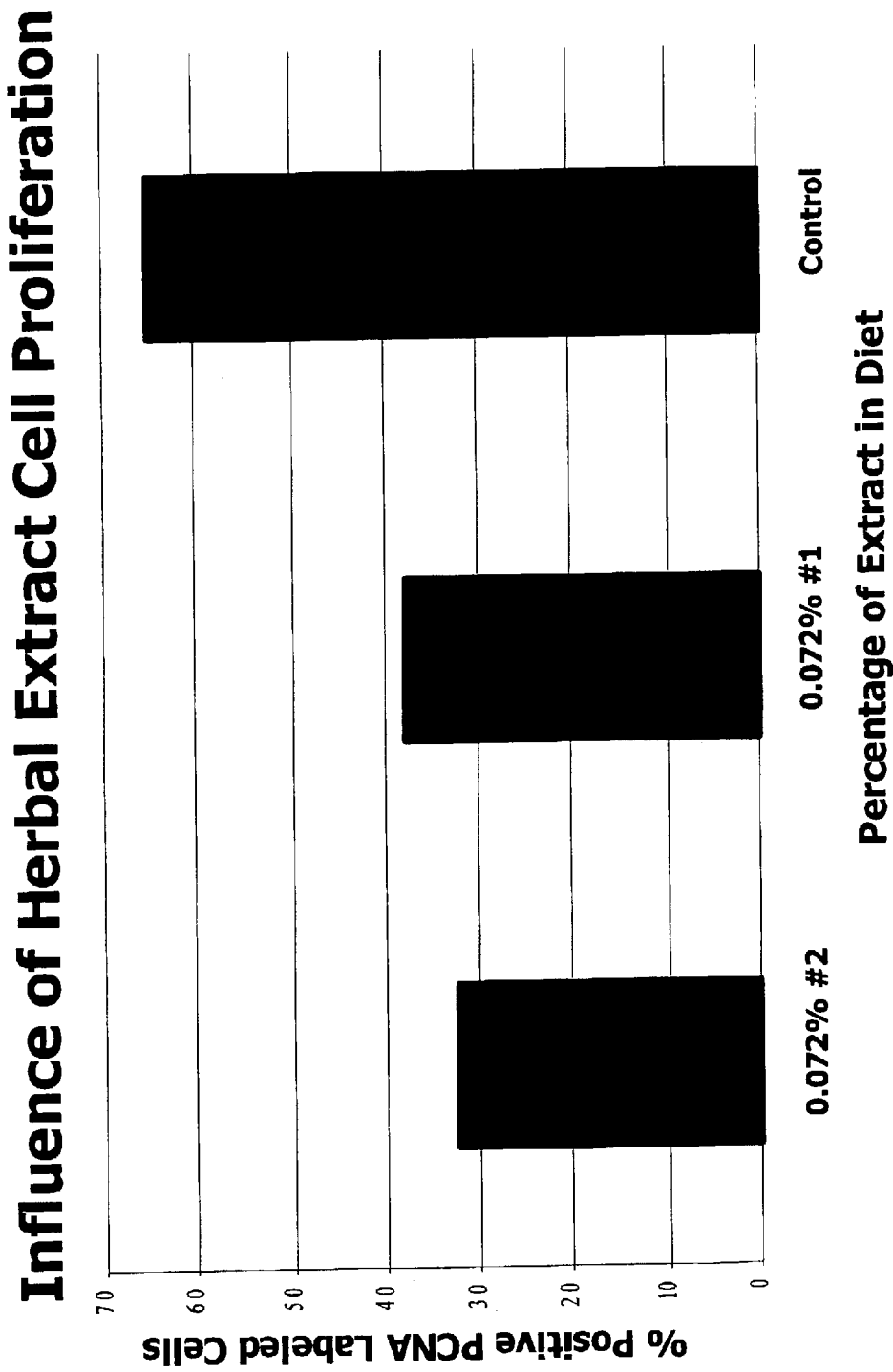
FIG. 15 shows the influence of herbal extract on tumor cell proliferation, as measured by PCNA as an indicator of cell proliferation rate, for selected animal groups in a third experiment with two different extract batches

FIG. 15. shows the influence of herbal extract on tumor cell proliferation, as measured by Proliferating Cell Nuclear Antigen (PCNA) as an indicator of cell proliferation rate, for selected animal groups. Thus, reductions in the percentages of PCNA positive cells with both the 0.072% (w/v) herbal extracts were roughly proportional to reductions in tumor weights for these same two dosages (60% and 50% reductions in PCNA for #1 and #2, respectively, versus 45% and 40% reductions in average tumor weights; FIG. 14).

EXAMPLE 4

Testing in Human Subjects

The following cases are illustrative of the experiences of many other patients who have used herbal extracts of the present invention, in the Philippines, Taiwan and Cambodia.

Case 1:

Male Patient A in the Philippines had a blood test that indicated that his Prostate Specific Antigen (PSA) level was 6.1. He was given 12 gm twice daily of the preferred embodiment shown in Table 2, except that no Ganodum (extract of *Ganoderma Lucidum*) was included. After 1 week his PSA level was reduced to 5.1. He was given the same dose of an extract identical to the above, except for the fact that Ganodum was included, as specified in Table 1, for another week, after which his PSA reading was 3.4. These results suggest that *Ganoderma Lucidum* taken with the herbal extract enhances the medicinal effect on PSA level.

Case 2:

Male Patient B in the Philippines had a blood test that showed his PSA level to be 5.2. He was given extract with Ganodum, as in Case 1, above, and his PSA was reduced to 3.4.

Case 3:

Male Patient C in the Philippines had a blood test that showed his PSA level to be 11.2. He was given a larger dose of extract including Ganodum (18 gm twice daily). After 1 week the PSA level was reduced to 10.6; and after two weeks, to 9.8. The patient then stopped taking the extract. After one month without extract, his PSA level increased to 10.7. Subsequent administration of extract became less effective (the PSA level remained high). Thus, after almost 2 months of additional administration of the extract, the PSA level gradually reduced again to only 9.8. This case suggests that extract should be continuously administered until an elevated PSA level is reduced to a normal.

Case 4:

Male Patient D in Taiwan had frequent urges to urinate in the night (nocturia). In a typical night; for instance, he had an urge to urinate at least 5 times. He was treated with various medications in Taiwan, Japan and China, but the situation did not improve. When he heard about the herbal extract of the invention, he took the same dose as in Case 2 (12 gm twice daily of the preferred embodiment shown in Table 2, including Ganodum) for one month. At the end of the month, the frequency of his urges to urinate was reduced to only about two times a night. No PSA test results are available for this subject.

All patents, patent applications and publications mentioned herein are hereby incorporated by reference in their entirety.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A pharmaceutical composition for treating or reducing the risk of prostate disorders comprising therapeutically effective amounts of the following herbal and other components:

Radix Asparagi; Radix Angelicae Pubescentis; Radix Trichosanthis; Radix Scuttellariae; Radix Angelicae Sinensis; Radix Dipsaci; Cortex Eucommiae; Medulla Junci; Rhizoma Anemarrhenae; Caulis Akebiae; Herba Dianthi; Semen Plantaginis; fried Cortex Phellodendri; Radix et Rhizoma Rhei; Rhizoma seu Radix Notopterygii; Olibanum; Fructus Gardeniae; Radix Astragali seu Hedysari; Rhizoma Cimicifugae; Radix Bupleuri; Myrrha; Gypsum Fibrosun; crude Radix Rehamanniae; Folium Pyrrosiae; Rhizoma Acori Graminei; Rhizoma Dioscoreae Hypoglaucae; Radix Linderae; Herba Cistanche; Radix Paeoniae Rubra; Rhizoma Dioscoreae; Semen Euryales; Cortex Mouton; Polyporus Umbellatus; Radix Rehmanniae Praeparata; Medulla Tetrapanacis; Semen Coicis; Poria Fructus Horedi Germinatus; Radix Aconiti Praeparata; Rhizoma Alismatis; Cortex Cinnamomi; Herba Asari; Radix Glycyrrhizae; Stigma Maydis; and *Phaseolus Radiatus* L.

2. The composition of claim 1, further comprising *Ganoderma Lucidum*.

3. The composition of claim 1, further comprising at least one herbal or other component selected from the following group of components:

Bulbus Lilii; Citri Reticulatae Viride; Cortex Moutan Radicis; Cortex Lycii Radicis; Faecs Trogropterori; Flos Lonicerae; Fructus Alpiniae Oxyphyllae; Fructus Aurantii Immaturus; Fructus Cnidii; Fructus Corni;

Fructus Schisandrae; Fructus Arctii; Herba Cynomorii; Herba Epimedii; Herba Leonuri; Herba Polygoni Avicularis; Radix Achyranthis Bidentatae; Radix Aconiti Kusnezoffii; Radix Angelicae Dahuricae; Radix Aucklandiae; Radix Clematidis; Radix Codonopsis Pilosulae; Radix Gentianae Macrophyllae; Radix Ophiopogonis; Radix Paeoniae Alba; Radix Polygalae; Radix Stephaniae Tetrandrae; Ramulus Cinnamomi; Rhizoma Atractylodis; Rhizoma Belamcandae; Rhizoma Corydalis; Rhizoma Ligustici Chuanxiong; Rhizoma seu Radix Nototerygii; Rhizoma Zingiberis Recens; Semen Biotae; Semen Cuscutae; Semen Dolichoris Album; Semen Pharbitidis; Semen Persicae; Spica Prunellae; and Stigma Maydis.

4. The composition of claim 1, comprising an aqueous or alcohol or aqueous-alcohol extract of each included herbal component.

5. The composition of claim 4, comprising an aqueous extract of the following herbal and other components in the specified ratios of dry weights compared to the dry weight of the least abundant component:

Radix Asparagi (6:1); Radix Angelicae Pubescentis (6:1); Radix Trichosanthis (9:1); Radix Scuttellariae (4:1); Radix Angelicae Sinensis (1:1); Radix Dipsaci (1:1); Cortex Eucommiae (1:1); Medulla Junci (1:1); Rhizoma Anemarrhenae (4:1); Caulis Akebiae (8:1); Herba Dianthi (8:1); Semen Plantaginis (6:1); fried Cortex Phellodendri (8:1); Radix et Rhizoma Rhei (4:1); Rhizoma seu Radix Notopterygii (1:1); Olibanum (1:1); Fructus Gardeniae (7:1); Radix Astragali seu Hedysari (15:1); Rhizoma Cimicifugae (4:1); Radix Bupleuri (4:1); Myrrha (1:1); Gypsum Fibrosun (18:1); crude Radix Rehamanniae (15:1); Folium Pyrrosiae (9:1); Rhizoma Acori Graminei (6:1); Rhizoma Dioscoreae Hypoglaucae (6:1); Radix Linderae (6:1); Herba Cistanche (1:1); Radix Paeoniae Rubra (6:1); Rhizoma Dioscoreae (9:1); Semen Euryales (6:1); Cortex Mouton (1:1); Polyporus Umbellatus (6:1); Radix Rehmanniae Praeparata (1:1); Medulla Tetrapanacis (6:1); Semen Coicis (8:1); Fructus Horedi Germinatus (Poria) (9:1); Radix Aconiti Praeparata (6:1); Rhizoma Alismatis (6:1); Cortex Cinnamomi (3:1); Herba Asari (4:1); Radix Glycyrrhizae (3:1); Stigma Maydis (18: 1); *Phaseolus Radiatus* L (31:1); and *Ganoderma Lucidum* (1:1).

6. The composition of claim 4, further comprising a pharmaceutically acceptable carrier, diluent or additive.

7. A dietary supplement comprising the composition of claim 1.

8. A composition of matter comprising a mixture of therapeutically effective amounts of the following herbal and other components:

Radix Asparagi; Radix Angelicae Pubescentis; Radix Trichosanthis; Radix Scuttellariae; Radix Angelicae Sinensis; Radix Dipsaci; Cortex Eucommiae; Medulla Junci; Rhizoma Anemarrhenae; Caulis Akebiae; Herba Dianthi; Semen Plantaginis; fried Cortex Phellodendri; Radix et Rhizoma Rhei; Rhizoma seu Radix Notopterygii; Olibanum; Fructus Gardeniae; Radix Astragali seu Hedysari; Rhizoma Cimicifugae; Radix Bupleuri; Myrrha; Gypsum Fibrosun; crude Radix Rehamanniae; Folium Pyrrosiae; Rhizoma Acori Graminei; Rhizoma Dioscoreae Hypoglaucae; Radix Linderae; Herba Cistanche; Radix Paeoniae Rubra; Rhizoma Dioscoreae; Semen Euryales; Cortex Mouton; Polyporus Umbellatus; Radix Rehmanniae Praeparata; Medulla Tetrapanacis; Semen Coicis; Poria Fructus Horedi Germinatus; Radix Aconiti Praeparata; Rhizoma Alismatis; Cortex Cinnamomi; Herba Asari; Radix Glycyrrhizae; Stigma Maydis; *Phaseolus Radiatus* L.; and *Ganoderma Lucidum*;

wherein said components are present in said mixture in amounts such that said mixture is effective in a mammal for treating or reducing the risk of a prostate disorder including prostatitis, benign prostate hyperplasia or prostatic carcinoma.

9. The composition of claim 8, wherein said mammal is a human being.

10. The composition of claim 9, wherein said mixture is effective for reducing serum levels of Prostate Specific Antigen (PSA) that are elevated above normal and for reducing irritative voiding symptoms of prostatitis.

11. The composition of claim 8, wherein said mixture is effective for ameliorating at least one effect of a prostate carcinoma in a mammal having such a tumor.

12. The composition of claim 11, wherein said ameliorating at least one effect of a prostate carcinoma comprises reducing the growth rate or mass of said carcinoma.

13. A method for treatment or reducing the risk of prostate disorders in a mammal including prostatitis, benign prostate hyperplasia and prostatic carcinoma, comprising administering to said mammal a composition of matter of claim 8 periodically for a time sufficient to achieve prevention or treatment of said conditions.

14. The method of claim 13, wherein said disorder is prostatic carcinoma and the administering is performed before surgery to remove said carcinoma.

15. The method of claim 13, wherein said administering periodically is conducted once or twice daily, or three to four times a week.

16. The method of claim 13, further comprising administering a therapeutically effective amount of an anticancer compound effective for prostate cancer, selected from the group consisting of luteinizing hormone releasing hormone, estrogen, antiandrogen, gonadotrophin-releasing hormone and synthetic analogs thereof which have hormone activity, or a therapeutically effective amount of a compound selected from the group consisting of antibiotics, antimetabolites and cytotoxic agents.

17. A method of ameliorating symptoms associated with prostate disorders in a mammal including prostatitis, benign prostate hyperplasia and prostatic carcinoma, comprising administering to said mammal a composition of matter of claim 8 periodically for a time sufficient to achieve the desired amelioration.

* * * * *